US012678226B2

(12) United States Patent
Murakami

(10) Patent No.: US 12,678,226 B2
(45) Date of Patent: Jul. 14, 2026

(54) HAIR REMOVAL DEVICE AND IRRADIATION POSITION CORRECTION METHOD

(71) Applicant: Eidea Inc., Tokyo (JP)

(72) Inventor: Tomohiro Murakami, Tokyo (JP)

(73) Assignee: EIDEA INC., Tokyo (JP)

( * ) Notice: Subject to any disclaimer, the term of this patent is extended or adjusted under 35 U.S.C. 154(b) by 275 days.

(21) Appl. No.: 18/278,889

(22) PCT Filed: Nov. 19, 2021

(86) PCT No.: PCT/JP2021/042635
§ 371 (c)(1),
(2) Date: Aug. 25, 2023

(87) PCT Pub. No.: WO2022/185627
PCT Pub. Date: Sep. 9, 2022

(65) Prior Publication Data
US 2024/0138912 A1 May 2, 2024

(30) Foreign Application Priority Data

Mar. 2, 2021 (JP) ................................. 2021-032629

(51) Int. Cl.
*A61B 18/20* (2006.01)
*A45D 44/00* (2006.01)
(Continued)

(52) U.S. Cl.
CPC ............ *A61B 18/203* (2013.01); *A45D 44/00* (2013.01); *A61B 34/20* (2016.02);
(Continued)

(58) Field of Classification Search
None
See application file for complete search history.

(56) References Cited

U.S. PATENT DOCUMENTS

| | | | |
|---|---|---|---|
| 7,108,690 B1 * | 9/2006 | Lefki | A61B 18/203 606/9 |
| 2015/0287190 A1 * | 10/2015 | Kim | G16H 20/40 382/128 |

(Continued)

FOREIGN PATENT DOCUMENTS

| | | |
|---|---|---|
| CN | 103354770 | 10/2013 |
| JP | 2002-541906 A | 12/2002 |

(Continued)

OTHER PUBLICATIONS

Extended European Search Report dated Apr. 25, 2024 for the corresponding European Application.

*Primary Examiner* — Unsu Jung
*Assistant Examiner* — Sefra D. Manos
(74) *Attorney, Agent, or Firm* — Clark Hill PLC; James R. Foley

(57) ABSTRACT

A hair removal device that performs hair removal treatment using light emitted from a light source, the hair removal device including: a light source unit including the light source; an irradiation position control mechanism configured to guide the light emitted from the light source unit to an irradiation scheduled position; an imaging unit configured to be able to image a predetermined region including the light emitted toward the irradiation scheduled position; and an irradiation position deviation amount detection unit configured to detect an irradiation position deviation amount between the irradiation scheduled position and a real irradiation position of the light, the hair removal device being configured to correct a guide position of the light by the irradiation position control mechanism by using the irradiation position deviation amount detected by the irradiation position deviation amount detection unit.

9 Claims, 13 Drawing Sheets

(51) Int. Cl.
    *A61B 18/00*        (2006.01)
    *A61B 34/20*        (2016.01)
    *A45D 26/00*        (2006.01)

(52) U.S. Cl.
    CPC ................... *A45D 2026/008* (2013.01); *A61B*
           *2018/00476* (2013.01); *A61B 2034/2055*
           (2016.02); *A61B 2034/2065* (2016.02)

(56)                References Cited

U.S. PATENT DOCUMENTS

2018/0344403 A1 \*  12/2018  Gündogdu ........... A61B 18/203
2022/0203115 A1 \*   6/2022  Gandman .............. G16H 50/20

FOREIGN PATENT DOCUMENTS

| | | |
|---|---|---|
| JP | 2004216418 | 8/2004 |
| JP | 2005-500879 A | 1/2005 |
| JP | 2006-095530 A | 4/2006 |
| KR | 20150116752 | 10/2015 |
| WO | 00/53261 A1 | 9/2000 |
| WO | 00/62700 A1 | 10/2000 |
| WO | 03/011159 A1 | 2/2003 |

\* cited by examiner

LIGHT BEAM

[ IN INITIAL SETTING ]

START

CLEAR $T_0$, $T_1$, $T_2$ ~S1

GENERATE COORDINATE SYSTEM CORRECTION DATA ~S2

COORDINATE SYSTEM CORRECTION PROCESS ~S3

SPECIFY (GENERATE) $C_0$ ~S4

IRRADIATE ~S5

CAPTURE IMAGE ~S6

DETECT IRRADIATION POSITION DEVIATION AMOUNT ~S7

STORE IN CORRESPONDING BLOCK OF $T_0$ ~S8

LAST $C_0$? S9

NO

YES

GENERATE $T_0$, $T_2$ ~S10

END

[IN CORRECTION(OUTSIDE OF TREATMENT PERIOD)]

START

CLEAR $T_1$ AND MAKE $T_2 = T_0$ —S11

SPECIFY (GENERATE) $C_0$ WITH REFERENCE TO $T_0$ —S12

IRRADIATE —S13

CAPTURE IMAGE —S14

DETECT IRRADIATION POSITION DEVIATION AMOUNT —S15

STORE IN CORRESPONDING BLOCK OF $T_1$ —S16

S17
LAST $C_0$?    NO    YES

GENERATE $T_1$ —S18

GENERATE $T_2$ USING $T_0$ AND $T_1$ —S19

END

[IN CORRECTION (DURING TREATMENT PERIOD)]

HAIR REMOVAL DEVICE AND IRRADIATION POSITION CORRECTION METHOD

TECHNICAL FIELD

The present invention relates to a hair removal device and an irradiation position correction method.

BACKGROUND ART

A conventional laser hair removal device is known that irradiates body hairs existing on human skin with laser light to remove the body hairs. All the existing commercialized epilators using laser light and light of flash lamps irradiate the entire skin with strong light in order to irradiate the body hairs having an area ratio on the skin of only about 1%, of which efficiency is very poor, which leads to an increase in device size and causes damage and risks to the skin. In addition, light is emitted regardless of the thicknesses of hair roots, the color of the hairs, the color of the skin and its depth, which cannot be said to be optimal.

In recent years, in order to solve such problems, a hair removal device that irradiates only hair roots of body hairs with laser light has been proposed (Patent Literature 1 or the like). The laser hair removal device of Patent Literature 1 is configured to specify the thicknesses (sizes) of the hair roots and the color of the hairs on the basis of an image obtained by imaging skin to be treated, and determine the dose of laser light to be emitted on the basis of the specified thicknesses of the hair roots and the specified color of the hairs. According to such a laser hair removal device of Patent Literature 1, it is possible to emit laser light at a dose suitable for the hairs to be treated, so that hair removal can be efficiently performed.

CITATION LIST

Patent Literature

Patent Literature 1: JP 2005-500879 A

SUMMARY OF INVENTION

Technical Problem

However, in the laser hair removal device described in Patent Literature 1, there is a possibility that an error occurs between a theoretical irradiation position and an actual irradiation position of the laser light due to mechanical factors generated in a detector (CMOS image sensor) that images an object to be treated, a laser beam operating device that guides laser light toward a hair to be treated, and the like. In a case where there is such an error, a problem occurs in which the hair to be treated cannot be irradiated with the laser light.

It is therefore an object of the present invention to provide a hair removal device and an irradiation position correction method that reliably enable irradiation of hairs to be treated with beam light.

Solution to Problem

In order to achieve such an object, a hair removal device according to the present invention is a hair removal device that performs hair removal treatment using light emitted from a light source, the hair removal device including: a light source unit including the light source; an irradiation position control mechanism configured to guide the light emitted from the light source unit to an irradiation scheduled position; an imaging unit configured to be able to image a predetermined region including the light emitted toward the irradiation scheduled position; and an irradiation position deviation amount detection unit configured to detect an irradiation position deviation amount between the irradiation scheduled position and a real irradiation position of the light, the hair removal device being configured to correct a guide position of the light by the irradiation position control mechanism by using the irradiation position deviation amount detected by the irradiation position deviation amount detection unit.

In the hair removal device according to the present invention, the irradiation position deviation amount detection unit may be configured to specify a center of the light by using irradiation state image data captured by the imaging unit and specify the center of the light as the real irradiation position of the light.

The hair removal device according to the present invention may further include a correction condition creation unit configured to specify a correction amount of the guide position of the light by the irradiation position control mechanism by using the irradiation position deviation amount detected by the irradiation position deviation amount detection unit.

In the hair removal device according to the present invention, the irradiation position deviation amount detection unit may be configured to generate a modification table by dividing a treatment target region into a plurality of blocks and assigning the irradiation position deviation amount to each of the blocks.

In the hair removal device according to the present invention, the correction condition creation unit may be configured to generate a modified correction table on the basis of an initial correction table that stores an initial correction amount of the guide position and the modification table generated by the irradiation position deviation amount detection unit.

In the hair removal device according to the present invention, the correction condition creation unit may be configured to generate a statistical modification table by using a plurality of the modification tables and generate the modified correction table by using the statistical modification table.

The hair removal device according to the present invention may further include a control mechanism drive control unit configured to control the irradiation position control mechanism, wherein the control mechanism drive control unit may be configured to correct the guide position of the light by the irradiation position control mechanism on the basis of the modified correction table.

In addition, an irradiation position correction method according to the present invention is an irradiation position correction method for correcting an irradiation position of light emitted from a light source, the irradiation position correction method including: an irradiation step of guiding the light to an irradiation scheduled position and irradiating the irradiation scheduled position; an imaging step of imaging a predetermined region including the light emitted toward the irradiation scheduled position; and an irradiation position deviation amount detection step of detecting an irradiation position deviation amount between the irradiation scheduled position and a real irradiation position of the light, a guide position of the light being corrected using the irradiation position deviation amount detected at the irradiation position deviation amount detection step.

In the irradiation position correction method according to the present invention, the irradiation step, the imaging step, and the irradiation position deviation amount detection step may be executed during a treatment period in which hair removal treatment is performed by the light emitted from the light source.

In the irradiation position correction method according to the present invention, the irradiation step, the imaging step, and the irradiation position deviation amount detection step may be executed outside of a treatment period in which hair removal treatment is performed by the light emitted from the light source.

Advantageous Effects of Invention

According to the present invention, it is possible to provide a hair removal device and an irradiation position correction method that reliably enable irradiation of hairs to be treated with beam light.

DESCRIPTION OF EMBODIMENTS

Hereinafter, a preferred embodiment for carrying out the present invention will be described with reference to the drawings. Note that the following embodiment is not intended to limit the invention according to each claim, and not all the combinations of features described in the embodiment are necessarily essential to the solution of the invention. In addition, the drawings are schematic drawings in which emphasis, omission, and ratio adjustment are appropriately performed in order to illustrate the present invention, and may be different from actual shapes, positional relationships, and ratios.

A hair removal device 1 according to the present embodiment is a hair removal device that irradiates body hairs existing on human skin with light from a light source to remove the body hairs permanently or over a long period of time (hair removal treatment).

Figure 1:
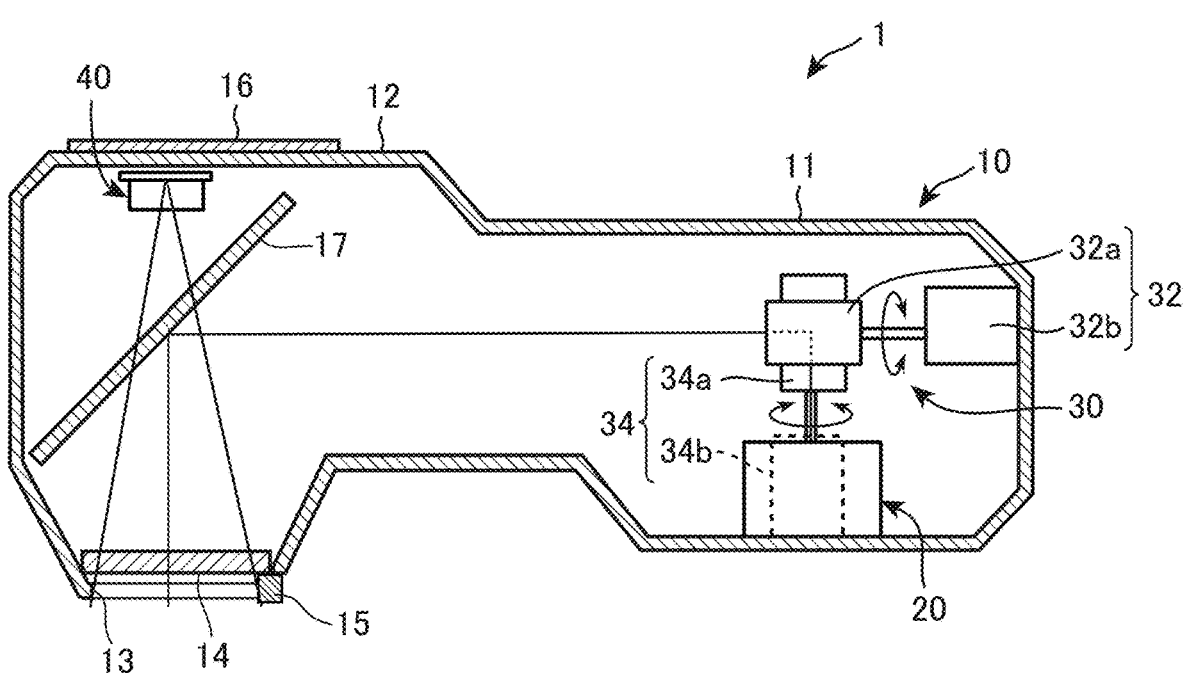
FIG. 1 is a diagram schematically illustrating a configuration of a hair removal device according to an embodiment of the present invention.

Specifically, as illustrated in FIG. 1, the hair removal device 1 includes a housing 10 that can be gripped by a user, a light source unit 20, an irradiation position control mechanism (for example, a control mechanism capable of controlling an irradiation position of a light beam in X and Y directions by disposing a galvano scanner including a turning mirror in two-axis X and Y directions) 30, and an imaging unit 40, which are housed in the housing 10, and a control unit 100 (see FIG. 3) that controls the light source unit 20 and the irradiation position control mechanism 30 on the basis of image data captured by the imaging unit 40. Note that the control unit 100 may be provided in the housing 10, or may be provided in another terminal connected to the housing 10 so as to enable wired or wireless data communication.

[Housing Configuration]

As illustrated in FIG. 1, the housing 10 includes a grip portion 11 that can be gripped by a user, and a head portion 12 that is continuously disposed on a distal end side of the grip portion 11. In the hair removal device 1 according to the present embodiment, the light source unit 20 and the irradiation position control mechanism 30 are disposed in the grip portion 11, and the imaging unit 40 is disposed in the head portion 12. However, the hair removal device 1 is not limited this configuration. In addition, a configuration and shape of the housing 10 are not limited to the illustrated example, and can be optionally changed.

The grip portion 11 is formed in an optional shape such as a tubular shape having such a diameter and a length in a longitudinal direction as to enable the user to grip the grip portion 11, and is designed in an outer shape suitable for making a skin facing surface of the head portion 12 face skin to be treated. As a result, the housing 10 facilitates positioning of the hair removal device 1 on the skin to be treated in a state in which the grip portion 11 is being gripped, and also facilitates movement of the hair removal device 1 from a treated region toward an untreated region. In addition, the grip portion 11 is provided with an irradiation button 18 (see FIG. 3) for switching ON/OFF irradiation by the light source unit 20.

The head portion 12 has an opening 13 in the skin facing surface (a lower surface in the present embodiment) facing the skin to be treated at the time of hair removal treatment, and is provided with a cover member 14 so as to cover the opening 13. The opening 13 has a size larger than a treatment target region of the skin to be treated with one shot (one shot). The cover member 14 has dust-proofness capable of preventing entry of dust or the like into the housing 10, and translucency at a level not hindering an irradiation process by the light source unit 20 and an imaging process by the imaging unit 40. As the cover member 14, for example, a transparent glass plate or the like can be used, but the cover member is not limited thereto.

In addition, a dichroic mirror 17 that further reflects beam light from the light source unit 20, which has been deflected by the irradiation position control mechanism 30, toward the outside of the opening 13 is provided inside the head portion 12. The dichroic mirror 17 is provided to be inclined at an angle of about 45 degrees with respect to the opening 13. The dichroic mirror 17 is a reflection surface that efficiently reflects irradiation light that is infrared light having a long wavelength, and is configured to efficiently reflect the beam light from the light source unit 20, which has been deflected by the irradiation position control mechanism 30, toward the outside of the opening 13 (the treatment target region of the skin) by the reflection surface. On the other hand, the dichroic mirror 17 can transmit visible light having a short wavelength with high transmittance in contrast with the irradiation light, and the imaging unit 40 is disposed on the transmission surface side. As a result, the imaging unit 40 can image the outside of the opening 13 (the treatment target region of the skin) with a small loss through the dichroic mirror 17.

Furthermore, illumination means (not illustrated) capable of emitting illumination light toward the opening 13 is provided inside the head portion 12. The illumination means is configured to light up at the time of imaging by the imaging unit 40 to illuminate the treatment target region of the skin through the opening 13. As such illumination means, various optional light sources such as a general-purpose LED can be used.

In addition, the head portion 12 is provided with a movement detection sensor 15 for detecting a movement amount of the hair removal device 1 with respect to the skin to be treated on the skin facing surface. The movement detection sensor 15 is provided at a position that is not hidden by the user's hand in a state where the user grips the grip portion 11, for example, near the opening 13. By providing such a movement detection sensor 15, for example, it is possible to monitor vibration (minute movement) during a treatment time in real time, and as a result, it is possible to perform a warning process such as prompting re-irradiation by an alarm sound and display in a case where a deviation amount is a certain amount or more. As the movement detection sensor 15, for example, an optical mouse sensor, an acceleration sensor, a gyrosensor, and the like can be used, but the movement detection sensor is not limited thereto.

Furthermore, the head portion 12 is provided with a display panel 16 on a surface facing the user side (an upper surface in the present embodiment) at the time of hair removal treatment. The display panel 16 is configured to be able to display a real-time video (live image) captured by the imaging unit 40 when, for example, the hair removal device 1 is moved from a treated region toward an untreated region. In this way, by displaying the live image on the display panel 16, it is possible to assist the movement of the hair removal device 1 to the untreated region. As the display panel 16, for example, a liquid crystal panel or the like can be used, but the display panel is not limited thereto.

[Configuration of Light Source Unit]

The light source unit 20 includes a beam-like high-brightness light source (not illustrated) having irradiation intensity (energy density) capable of sufficiently damaging hair roots and removing hairs permanently or over a long period of time (hair removal treatment). As such a light source, for example, various known light sources such as a laser, a semiconductor laser, a diode-pumped solid-state laser, a solid-state laser, and a super-bright LED can be optionally adopted.

The beam light emitted from the light source preferably has a diameter necessary and sufficiently large for one hair root on an irradiation surface. That is, the beam diameter of the beam light emitted from the light source is preferably set to be larger than a diameter of a hair root or a pore in consideration of image recognition accuracy, positioning accuracy (position deviation) of a scanner, and the like.

The light source unit 20 is preferably configured to be able to adjust the irradiation intensity (power, dose) of the light source within a predetermined range (for example, 1 to 100 $J/cm^2$). In particular, the light source unit 20 is preferably configured to be able to irradiate each hair with the beam light by selecting optimal irradiation intensity according to a pore size, a hair color, and a skin color around the pore of each hair to be treated. As a method of controlling the irradiation intensity of the light source, various known methods such as controlling of power output itself and controlling of a pulse width can be adopted. In addition, in the present specification, the term "pore size" includes all of a case of referring to the size (thickness) of the pore itself, a case of referring to the thickness of the hair, and a case of referring to the total size of the pore and the hair.

In addition, it is preferable that the light source unit 20 includes a plurality of (for example, three types of) light sources having different wavelengths from each other, and includes multiplexing means (not illustrated) for appropriately combining light emitted from the plurality of light sources. In this case, the plurality of light sources may include a first light source (not illustrated) capable of emitting beam light having a relatively short wavelength (for example, about 755 nm) that is easily absorbed by melanin pigment contained in a large amount in the hair, a third light source (not illustrated) capable of emitting beam light having a relatively long wavelength (for example, about 1064 nm) that is relatively less absorbed by the melanin pigment and is gentle to the skin, and a second light source capable of emitting beam light having a wavelength (for example, about 810 nm) between the first light source and the third light source. In addition, as the multiplexing means, various known means such as, for example, a wavelength selection mirror (dichroic mirror), a wavelength selection prism (dichroic prism), a polarizing beam splitter (PBS), and a polarizing plate can be adopted.

According to such a configuration, the irradiation can be performed in a state in which the light sources having a plurality of wavelengths are combined with optional intensity, which makes it possible to select not only the irradiation intensity but also an optimal wavelength combination according to information on the pore size, the hair color, and the skin color around the pore of each hair to be treated, to irradiate each hair with the beam light.

Although the light source unit 20 is disposed in the grip portion 11 of the housing 10 in the example illustrated in FIG. 1, the light source unit is not limited to this configuration. The light source unit 20 can be disposed at any position in the housing 10 as long as the light can be emitted from the opening 13 of the housing 10 through the irradiation position control mechanism 30 or the like.

[Configuration of Irradiation Position Control Mechanism]

The irradiation position control mechanism 30 is beam light deflecting means (scanning means) for guiding the beam light emitted from the light source unit 20 to an irradiation scheduled position (a corrected guide position C' in a case where the irradiation scheduled position is corrected) on the treatment target region (an X-Y plane to be a treatment range) of the skin on the basis of a control signal from a control mechanism drive control unit 122 to be described later of the control unit 100. Specifically, as illustrated in FIGS. 1 and 2, the irradiation position control mechanism 30 includes an X-direction deflection unit 34 for moving the beam light emitted from the light source unit 20 in an X direction (first direction) on the treatment target region of the skin, and a Y-direction deflection unit 32 for moving the beam light in a Y direction (second direction perpendicular to the first direction) on the treatment target region of the skin.

Figure 2:
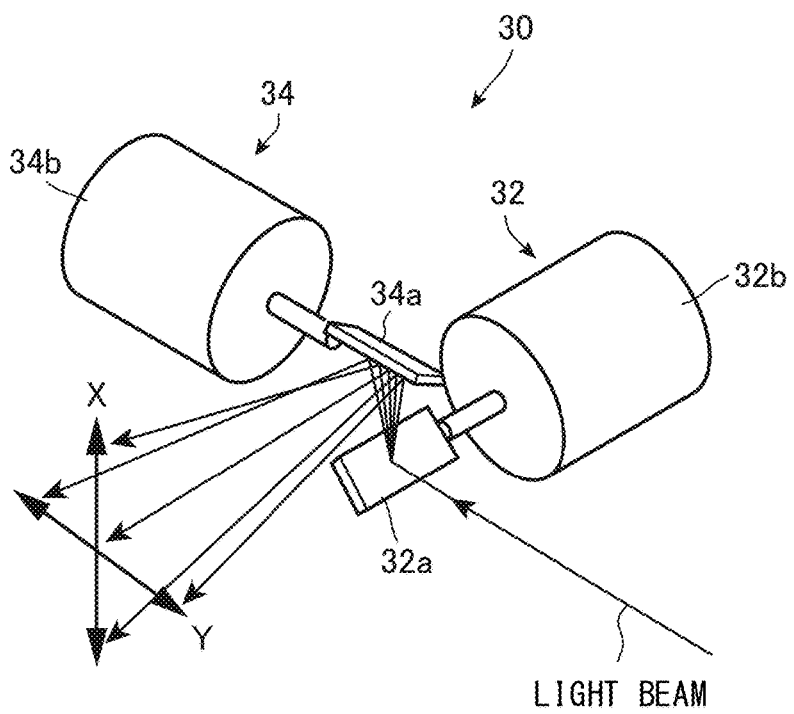
FIG. 2 is a diagram schematically illustrating a configuration of an irradiation position control mechanism.

As illustrated in FIGS. 1 and 2, the Y-direction deflection unit 32 and the X-direction deflection unit 34 include reflection mirrors 32a and 34a capable of reflecting the beam light, and drive units 32b and 34b that change inclination angles of the reflection mirrors 32a and 34a. The Y-direction deflection unit 32 is disposed so as to reflect the beam light emitted from the light source unit 20 toward the X-direction deflection unit 34, and the X-direction deflection unit 34 is disposed so as to further reflect the beam light reflected by the Y-direction deflection unit 32 toward the dichroic mirror 17. In addition, the Y-direction deflection unit 32 and the X-direction deflection unit 34 are disposed such that a rotation axis of the reflection mirror 32a of the Y-direction deflection unit 32 and a rotation axis of the reflection mirror 34a of the X-direction deflection unit 34 are perpendicular to each other. With such a configuration, the irradiation position control mechanism 30 is configured to be able to position the beam light emitted from the light source unit 20 at the irradiation scheduled position on the treatment target region (the X-Y plane to be the treatment range) of the skin by individually controlling the inclination angles of the reflection mirrors 32a and 34a of the X-direction deflection unit 34 and the Y-direction deflection unit 32.

As the X-direction deflection unit 34 and the Y-direction deflection unit 32, for example, a galvano scanner (electromagnetic method), a servo motor (electromagnetic method), a MEMS mirror (electromagnetic force or electrostatic force), other deflectors that tilt a mirror by electromagnetic force or electrostatic force, or the like can be optionally used, and various known configurations such as an AO (Acousto-Optics) deflector (acousto-optical means) can also be adopted.

[Configuration of Imaging Unit]

As illustrated in FIG. 1, the imaging unit 40 is disposed on the transmission surface side of the dichroic mirror 17, and is configured to be able to image the treatment target region of the skin through the dichroic mirror 17 and the opening 13. The imaging unit 40 is preferably a 4K camera having 4K resolution, but is not limited thereto, and may be any means having the number of pixels capable of imaging pores in a visual field with sufficient resolution. As the imaging unit 40, for example, various known imaging means such as a CMOS sensor, a CCD sensor, an array sensor, and an imaging tube can be optionally adopted.

[Configuration of Control Unit]

Figure 3:
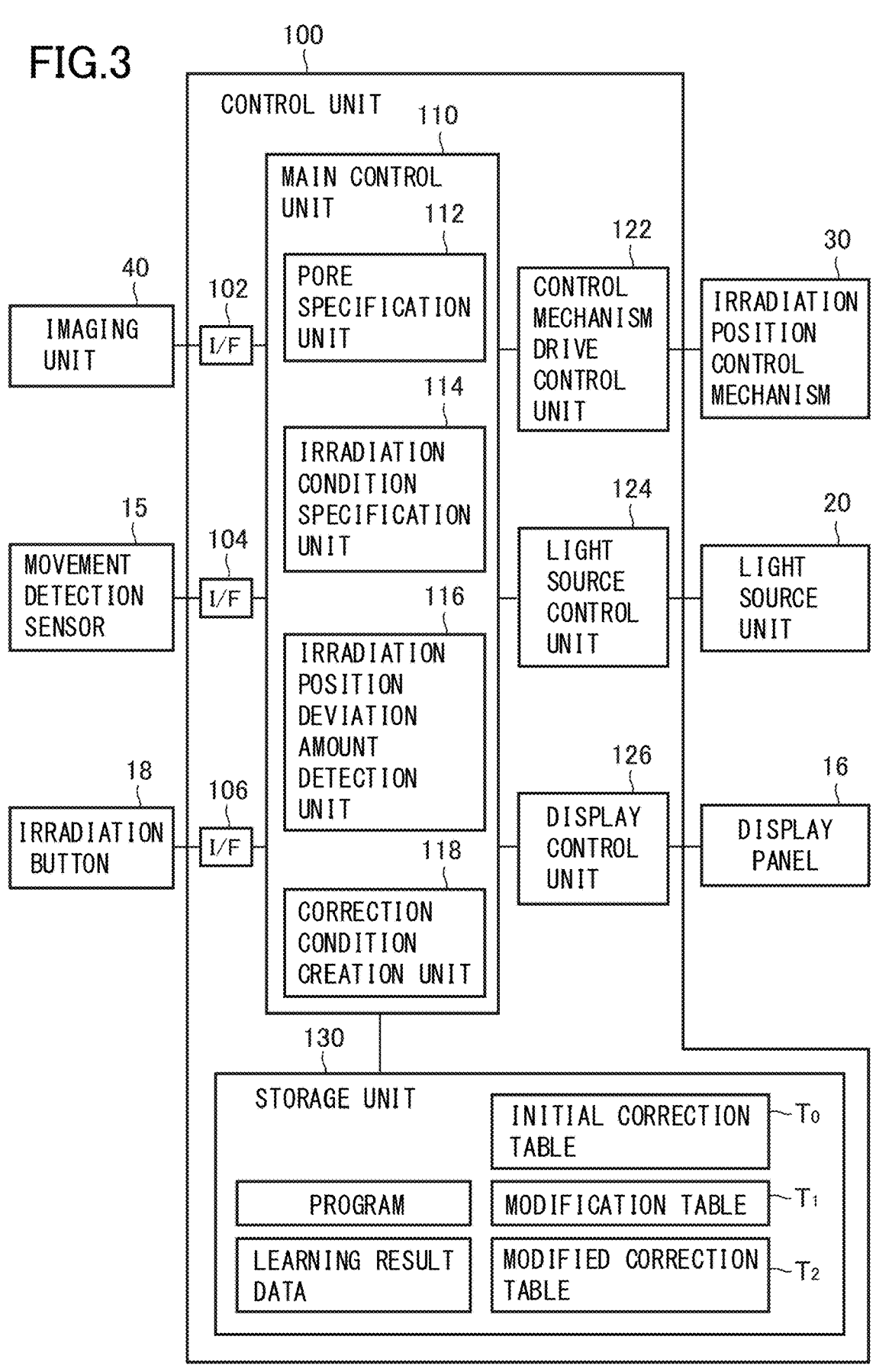
FIG. 3 is a diagram schematically illustrating a configuration of a control unit.

As illustrated in FIG. 3, the control unit 100 includes external interfaces 102, 104, and 106 for connecting with devices such as the imaging unit 40, the movement detection sensor 15, and the irradiation button 18, a main control unit 110 that performs arithmetic processing or the like for operating the hair removal device 1, the control mechanism drive control unit 122 that controls the irradiation position control mechanism 30, a light source control unit 124 that controls the light source unit 20, a display control unit 126 that controls the display panel 16, and a storage unit 130 that stores various data and information necessary for the hair removal treatment. In addition, the control unit 100 further includes a communication processing unit (not illustrated) capable of communicating with an external network.

The external interface 102 is an interface for connecting with the imaging unit 40, the external interface 104 is an interface for connecting with the movement detection sensor 15, and the external interface 106 is an interface for connecting with the irradiation button 18. Note that the external interface provided in the hair removal device 1 is not limited to these interfaces, and can be optionally provided according to a device to be connected. In addition, since a known interface according to the device to be connected can be used as the external interfaces 102, 104, and 106, a detailed description thereof is omitted.

The storage unit 130 is a memory including, for example, a RAM, a ROM, and the like, and stores a program including a command for operating the main control unit 110, learning result data for performing setting of a trained learner (a pore specification unit 112 and an irradiation condition specification unit 114 to be described later), and the like. Note that the storage unit 130 may include a RAM and a ROM described below included in the main control unit 110.

The main control unit 110 includes a CPU, which is a hardware processor, a RAM, a ROM, and the like, and is configured to deploy the program stored in the storage unit 130 in the RAM, and interpret and execute the program by the CPU, thereby achieving respective functions of the pore specification unit 112, the irradiation condition specification unit 114, an irradiation position deviation amount detection unit 116, and a correction condition creation unit 118 to be described later. Note that the CPU is preferably a high-performance processor (high-speed CPU) capable of executing deep learning (DL). In addition, the main control unit 110 may include a plurality of hardware processors, and the hardware processors may include a GPU (including a CPU-integrated GPU), an FPGA, and the like.

The pore specification unit 112 is configured to specify pores existing in the treatment target region on the basis of the image data of the treatment target region captured by the imaging unit 40. Specifically, the pore specification unit 112 is configured to acquire image data I (see FIG. 8) of a treatment target region TA (see FIG. 8) captured by the imaging unit 40 via the external interface 102, perform preprocessing on the image data I as necessary, and then extract pore candidates (pore candidates P (see FIG. 8)) existing in the treatment target region TA from the image data I by image analysis. Examples of the preprocessing include, but are not limited to, a process of enhancing pores by applying a minimum value filter to a 4K image, and a process of thinning unnecessary information to obtain a 2K image in order to reduce a burden of subsequent processing. In the following, the term "image data I" (in the case of adding a reference sign "I" to "image data") includes not only the original image data captured by the imaging unit 40 but also the processed image data preprocessed by the pore specification unit 112.

Here, it is preferable that the extraction of the pore candidates P by the pore specification unit 112 is executed by image processing (AI image recognition) using AI such as deep learning (DL). Specifically, since the original image data is a huge image having, for example, 4K×2K pixels and is not suitable for DL processing as it is, inference is performed by dividing the image into small regions (cells) such as 256×256 pixels. The pore specification unit 112 may include a trained learner (neural network) that has been trained so as to minimize an objective function including an inference value of XY coordinates of a pore in the small region, an inference value of a certainty factor to be a pore, and the like. The pore specification unit 112 may be configured to extract the pore candidates P by sequentially inputting, to the learner, images of the small regions (cells) obtained by dividing the image data I of the treatment target region TA captured by the imaging unit 40, and acquiring, from the learner, a certainty factor and coordinates of a pore candidate included in the image of the small region and having a high certainty factor to be a pore. Since this method does not include image processing by binarization that is a conventional technique at all, this method is less likely to be affected by detection accuracy due to luminance of a captured image, a pore direction, and the like, and pores having various different shapes and sizes can be detected with high accuracy. By extracting the pore candidates P by the AI image recognition as described above, it is possible to recognize small pores (such as vellus hairs) having low contrast and being difficult to detect as well as to measure by typical image processing.

In the present embodiment, examples of the trained learner include, but are not limited to, a learner obtained by fine-tuning (Fine-tuning) a convolutional neural network (for example, ResNet-50) trained by ImageNet or the like.

Instead of the configuration of extracting the pore candidates P by the AI image recognition, for thick black pores with sufficient contrast or the like, the pore specification unit 112 can optionally adopt, for example, a method of extracting the pore candidates P by a binarization process, threshold determination, or the like on the image data I of the treatment target region TA captured by the imaging unit 40.

The irradiation condition specification unit 114 is configured to specify irradiation conditions (irradiation intensity, wavelength, and the like) of the beam light from the light source unit 20 for each pore (pore candidate P) specified by the pore specification unit 112. Specifically, for each pore (pore candidate P) specified by the pore specification unit 112, the irradiation condition specification unit 114 is configured to first cut out an image (cutout pore image CI) including the pore and the skin around the pore from the image data I, and classify the cutout pore image CI into one having the highest certainty factor among a plurality of standard model images with different pore sizes, hair colors, and skin colors around the pore.

Here, each cutout pore image CI is formed such that the pore candidate P is located substantially at the center and the skin is present around the pore candidate P. In addition, similarly to the cutout pore image CI, the standard model image is an image including one or a plurality of pores and the skin around the pore(s). The plurality of standard model images having different pore sizes, hair colors, and skin colors around the pore are prepared in advance and stored in the storage unit 130 or the like. In association with each standard model image, optimal irradiation conditions (irradiation intensity, wavelength, and the like) of the beam light are registered from the viewpoints of epilation efficiency, safety (burn risk), and the like for a treatment target having the pore size, the hair color, and the skin color around the pore of the standard model image. Note that the irradiation intensity tends to be set to a larger value as the pore is thicker, the hair color is lighter, and the skin color is lighter, and the wavelength tends to be set to a shorter wavelength as the pore is thicker, the hair color is lighter, and the skin color is lighter.

The irradiation condition specification unit 114 is configured to specify the irradiation conditions (irradiation intensity, wavelength, and the like) of the beam light set in advance for the standard model image into which the cutout pore image CI is classified, as the irradiation conditions (irradiation intensity, wavelength, and the like) of the beam light for the pore (pore candidate P) of the cutout pore image CI.

It is preferable that the classification by the irradiation condition specification unit 114 is executed by image processing (AI image recognition) using AI such as deep learning (DL). Specifically, the irradiation condition specification unit 114 may include a trained learner (neural network) that has been trained so as to minimize an objective function including an inference value indicating the hair thickness (pore size), an inference value indicating the hair color, an inference value indicating the skin color, and the like, and may be configured to classify the cutout pore image CI into the standard model image that is generally most similar among the plurality of standard model images by inputting the cutout pore image CI to the learner and acquiring information of the pore candidate P included in the cutout pore image CI and the standard model image having the highest certainty factor (highest score) from the learner. In this case, the learner may execute a process of determining that there is no image similar to the cutout pore image CI (unclassifiable) among the standard model images prepared in advance and determining that the pore candidate P of the cutout pore image CI is not a pore (error determination) in a case where all the standard model images significantly fall below a predetermined certainty factor.

The irradiation position deviation amount detection unit 116 is configured to detect an irradiation position deviation amount ($\Delta X$, $\Delta Y$) between the irradiation scheduled position of the beam light and a real irradiation position of the beam light actually emitted toward the irradiation scheduled position. That is, the irradiation position deviation amount detection unit 116 is configured to be able to detect an error between a theoretical irradiation position and an actual irradiation position of the beam light, which is caused by mechanical factors (for example, accuracy of a sensor that measures a rotation angle, linearity, accuracy of a galvano motor, a servomotor, or the like, a cosine error for converting the rotation angle into linear coordinates, and an error in a mounting angle of a reflection mirror or the like) in the irradiation position control mechanism 30 or mechanical factors (for example, aberration of a lens or the like, and deviation in mounting positions of the irradiation position control mechanism 30 and the imaging unit 40) in the imaging unit 40.

Figure 4A:
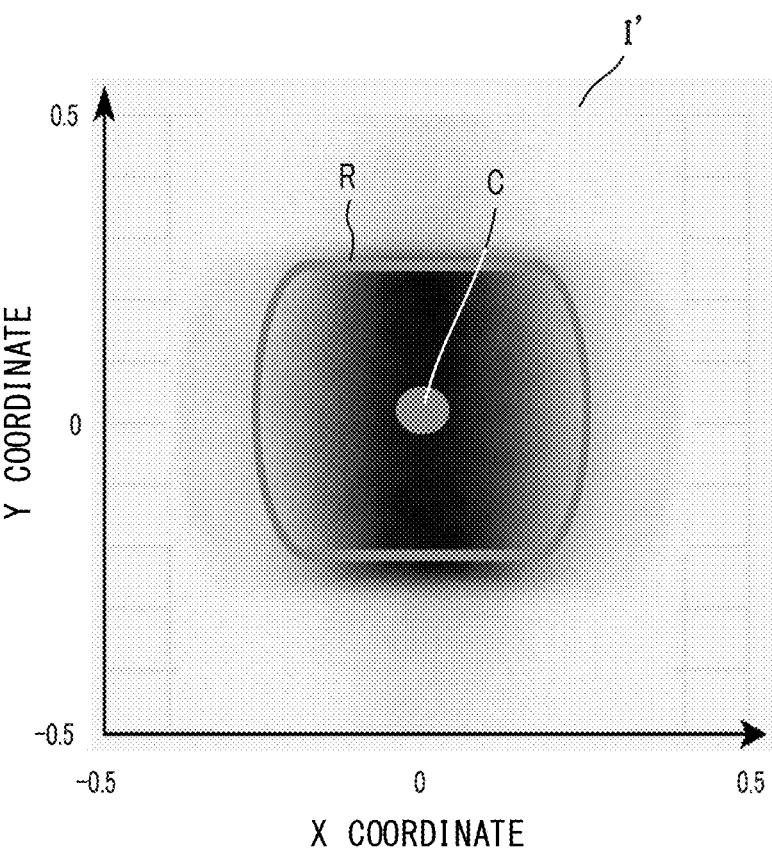
FIG. 4A is a diagram illustrating irradiation state image data obtained by imaging beam light.

Specifically, first, the irradiation position deviation amount detection unit 116 is configured to be able to execute a process of specifying a center C of the beam light by using irradiation state image data I' of the beam light obtained by imaging a predetermined region (the irradiation state) including the beam light emitted toward the irradiation scheduled position by the imaging unit 40 as illustrated in FIG. 4A.

At this time, it is preferable that the imaging unit 40 images an irradiation target portion such that a coordinate value of an irradiation scheduled position (theoretical irradiation position) $C_0$ of the beam light on the irradiation state image data I' can be specified. For example, it is preferable to image the irradiation target portion with the irradiation scheduled position $C_0$ of the beam light as an origin (0, 0) of the irradiation state image data I' as illustrated in FIG. 4B, but the imaging unit is not limited to this configuration.

Note that the irradiation state image data I' (second image data) is, for example, image data of a predetermined region centered on the irradiation scheduled position $C_0$ of the beam light, and is not limited to a particular size as long as the beam light fits. However, from the viewpoint of high-speed processing, the irradiation state image data I' (second image data) is preferably smaller in size (the number of pixels) than the image data I (first image data) captured to specify the pores by the pore specification unit 112, and more preferably has a narrow range including the irradiation scheduled position $C_0$.

In addition, the center C of the beam light can be specified by various optional methods such as a center search by gray search, fitting to a Gaussian function or the like, and a method of calculating the center of gravity of a place with high luminance. Examples thereof include image processing in which peak luminance of the emitted beam light is detected, and the position of the center of gravity of a range R (see FIG. 4A) extracted using ½ of the peak luminance as a threshold is obtained, and this position is set as the center C of the beam light.

Figure 4B:
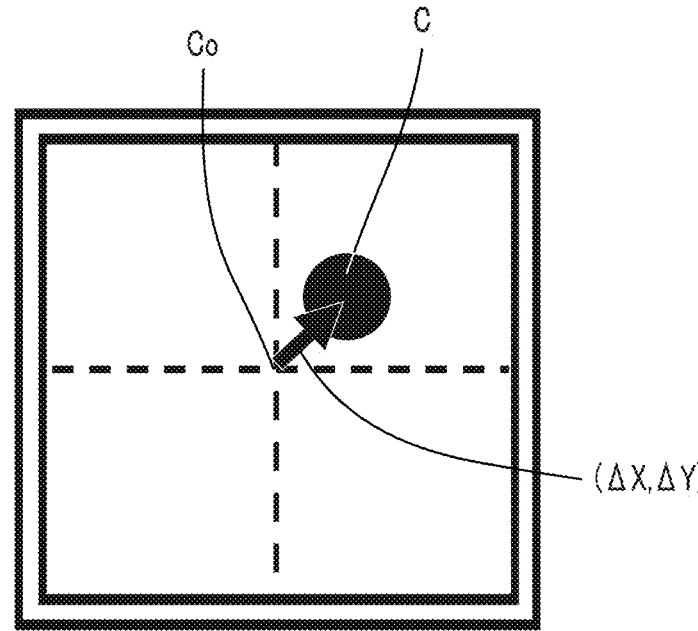
FIG. 4B is a diagram illustrating an image of an irradiation position deviation amount.

After specifying the center C of the beam light, the irradiation position deviation amount detection unit 116 is configured to be able to execute a process of calculating a difference between the coordinate value of the irradiation scheduled position (theoretical irradiation position) $C_0$ of the beam light and a coordinate value of the center C of the beam light on the irradiation state image data I', and specifying the difference as the error between the theoretical irradiation position and the actual irradiation position (real irradiation position) of the beam light caused by the mechanical factors or the like, that is, the irradiation position deviation amount ($\Delta X$, $\Delta Y$) as illustrated in FIG. 4B. The irradiation position deviation amount may be specified by pixel conversion.

Note that the detection of the irradiation position deviation amount ($\Delta X$, $\Delta Y$) by the irradiation position deviation amount detection unit 116 can be executed at any one or some of the time of factory shipment, the time of standby, and during a treatment period (during an actual hair removal treatment on the pores), and the timing is not particularly limited. In addition, the frequency of detecting the irradiation position deviation amount by the irradiation position deviation amount detection unit 116 can be optionally set.

Figure 5A:
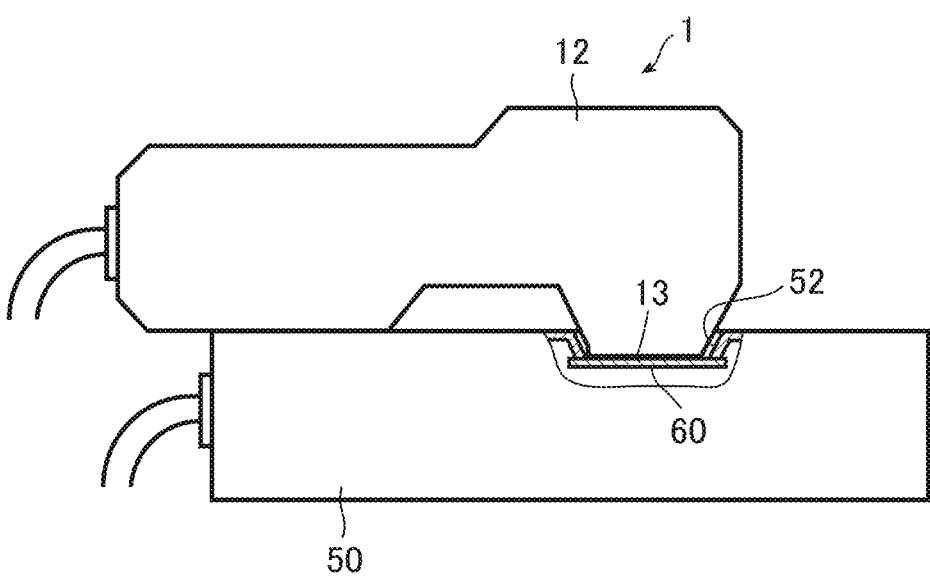
FIG. 5A is a diagram illustrating a state in which a reference reflection plate is disposed facing an opening of the hair removal device.
Figure 5B:
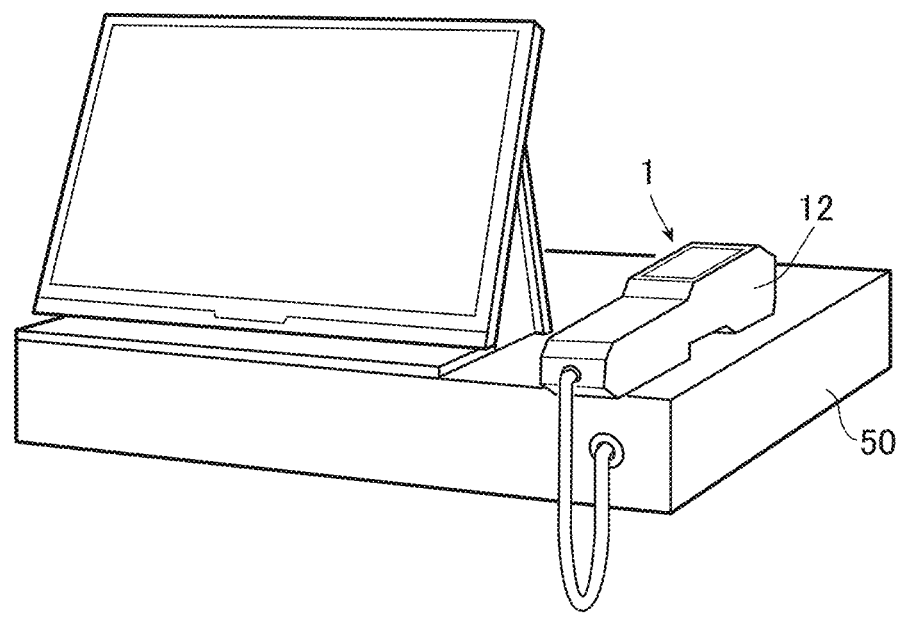
FIG. 5B is a diagram illustrating a state in which the hair removal device is placed on a hair removal device placement stand.

Here, in a case where the detection of the irradiation position deviation amount is executed outside of the treatment period (for example, at the time of factory shipment or standby), a reference reflection plate 60 and the like are disposed facing the opening 13 of the head portion 12 so as to be relatively unmovable as illustrated in FIG. 5A, so that the detection can be executed by setting a region (exposed region) of the reference reflection plate 60 exposed to the opening 13 as the treatment target region, and setting a predetermined portion in the exposed region of the reference reflection plate 60 as the irradiation target portion (irradiation scheduled position $C_0$). Examples of a method of disposing the reference reflection plate 60 in the opening 13 of the head portion 12 so as to be relatively unmovable include, but are not limited to, a method of forming a fitting recess 52 into which the head portion 12 of the hair removal device 1 can be fitted, in a hair removal device placement stand 50 and disposing the reference reflection plate 60 in the fitting recess 52, for example, as illustrated in FIG. 5B, and a method of covering the opening 13 of the head portion 12 with a lid (not illustrated) equipped with the reference reflection plate 60.

Figure 6A:
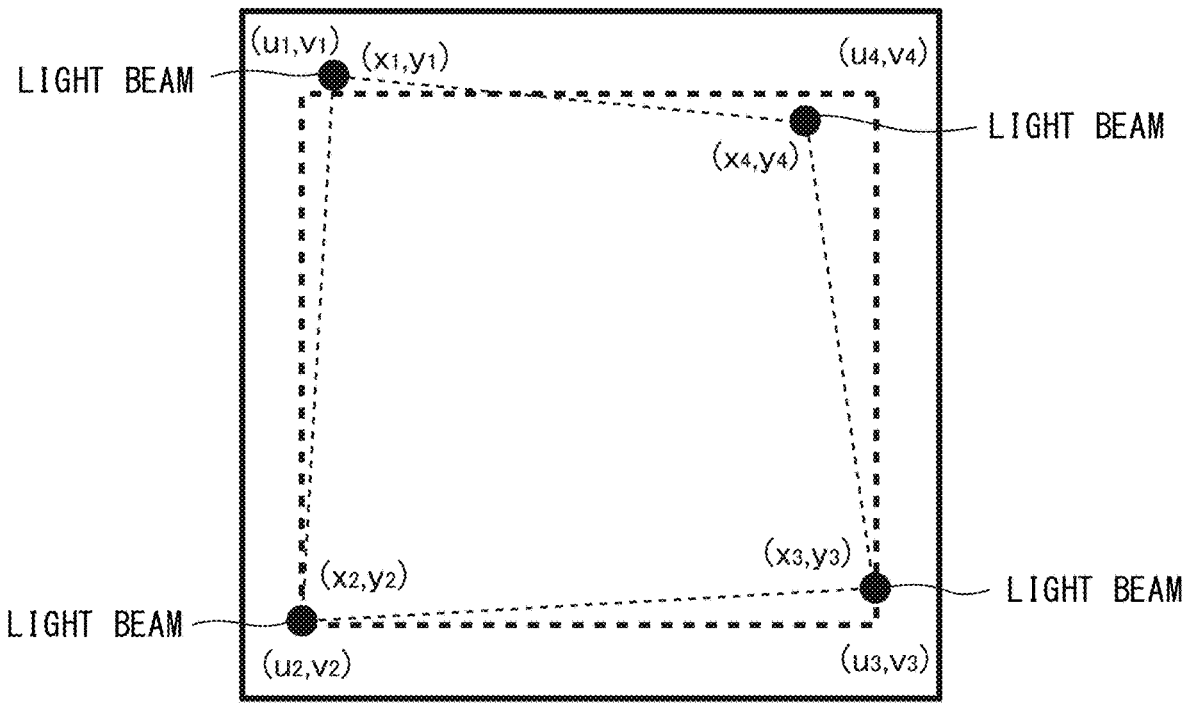
FIGS. 6A and 6B are diagrams illustrating a coordinate system correction process for correcting a deviation between a coordinate system of an imaging unit and a coordinate system of the irradiation position control mechanism.
Figure 6B:
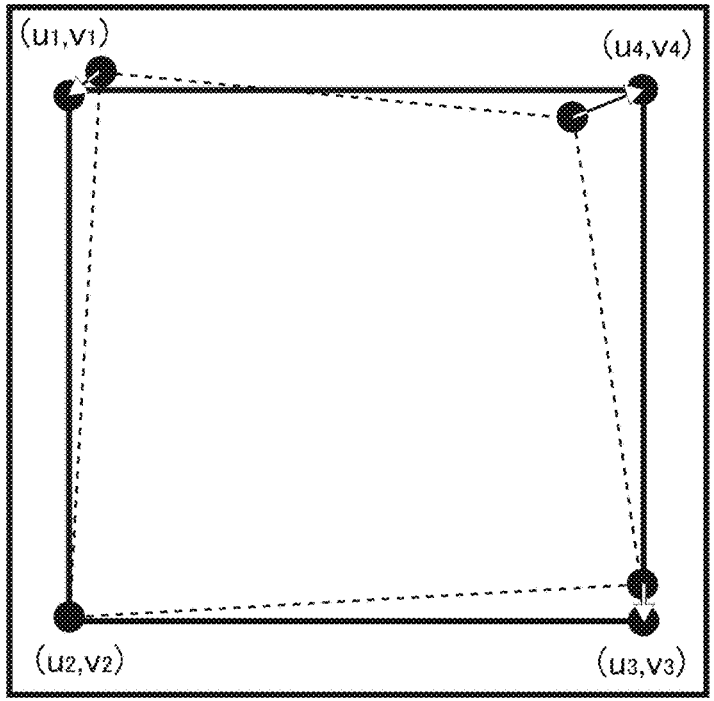

In a state in which the reference reflection plate 60 is disposed facing the opening 13, the irradiation position deviation amount detection unit 116 first executes a coordinate system correction process (numerical correction) for correcting an overall deviation between a coordinate system of the imaging unit 40 (camera) and a coordinate system of the irradiation position control mechanism 30 (laser scan). Examples of such a coordinate system correction process include a method of sequentially emitting beam light onto four corners in a state in which a scan range is limited within a visual field in consideration of the deviation as illustrated in FIG. 6A, calculating coordinates of the position of the center C (spot) of each beam light, and calculating correction data as illustrated in FIG. 6B. In FIGS. 6A and 6B, "xn, yn" (n=1, 2, 3, and 4) means coordinates (coordinates before conversion) of the irradiation position control mechanism 30 (laser scan), and "un, vn" (n=1, 2, 3, and 4) means coordinates (coordinates after conversion) of the imaging unit 40 (camera).

As such correction, for example, quadrilateral correction can be adopted, but the correction is not limited thereto. Various methods such as simpler scaling correction and parallelogram correction (affine transformation) can be adopted. Since specific calculation formulas of the quadrilateral correction, the scaling correction, the parallelogram correction, and the like are known, a description thereof is omitted. In addition, in a case where a temporal change of the overall deviation between the coordinate system of the imaging unit 40 (camera) and the coordinate system of the irradiation position control mechanism 30 (laser scan) is sufficiently small, the quadrilateral correction may be performed only at the time of factory shipment, overhaul, repair, or the like. In addition, in a case where each member has high assembly accuracy and no quadrilateral correction is required, the quadrilateral correction may be omitted and only the following processes described below may be performed.

Figure 7:
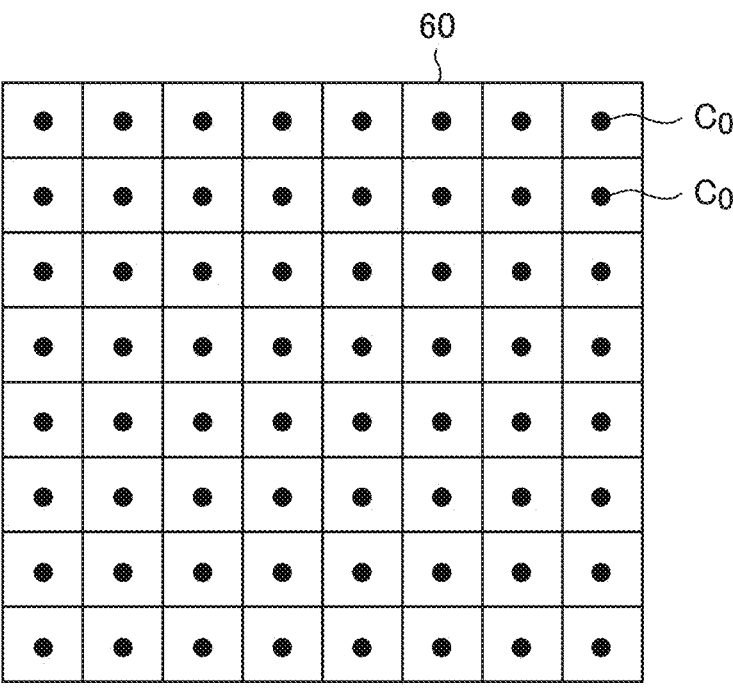
FIG. 7 is a diagram illustrating a state in which a region of the reference reflection plate exposed to the opening of the hair removal device is divided into a plurality of regions.

In addition, after executing the above-described coordinate system correction process, the irradiation position deviation amount detection unit 116 divides the exposed region of the reference reflection plate 60 into a plurality of regions, and detects the irradiation position deviation amounts for all the divided regions with the center of each of the divided regions as the irradiation scheduled position $C_0$ as illustrated in FIG. 7. However, the irradiation position deviation amount detection unit is not limited to this configuration, and may be configured to detect the irradiation position deviation amounts for limited divided regions (for example, divided regions located at four corners and a divided region located at the center). Note that the number of divisions of the exposed region in this case is preferably the same as the number of divisions (M×N) of an initial correction table $T_0$ and a modification table $T_1$ to be described later, but the number of divisions is not limited thereto. In addition, at the time of this re-photographing, the beam light is preferably emitted with lower irradiation intensity (power) than that at the time of executing the hair removal treatment in order to prevent halation.

In a case where the detection of the irradiation position deviation amount is executed at the time of standby, the irradiation position deviation amount detection process can be executed at any timing such as, for example, at the time of factory shipment, at the time of overhaul, at the time of repair, every several days, at the time of power startup, after completion of the prescribed number of times of treatment, and after completion of every treatment. In addition, the irradiation scheduled position $C_0$ can be optionally selected according to the correction frequency and the deviation amount. Details of the irradiation position correction executed at these timings will be described later.

On the other hand, in a case where the detection of the irradiation position deviation amount is executed during the treatment period, the detection can be executed by setting a skin surface (exposed region) exposed to the opening 13 as the treatment target region, and setting a predetermined portion in the exposed region of the skin surface as the irradiation target portion (irradiation scheduled position $C_0$). The irradiation position correction during the treatment period may not be expected to be highly accurate when performed once as compared with the above-described correction method using the reference reflection plate 60. Therefore, it is preferable to detect a small irradiation position deviation amount with respect to the irradiation scheduled position $C_0$ with reference to a modified correction table $T_2$. In addition, since it is necessary to consider a position deviation due to a curvature of the skin surface and a time lag (timing deviation) between imaging and beam light irradiation, it is preferable to modify the modification table $T_1$ and the modified correction table $T_2$ by performing imaging a plurality of times on the same spot and calculating the irradiation position deviation amount by statistical processing without directly adopting the irradiation position deviation amount obtained by performing imaging once. The irradiation position deviation amount detection process can be executed at any timing such as, for example, every shot, once every several shots, every treatment start, at the time of power startup, and every several days.

Figure 8:
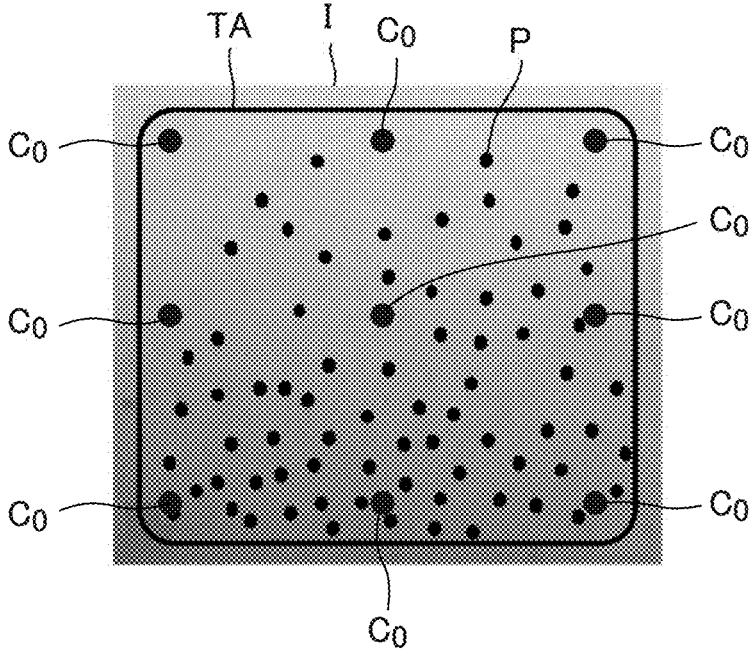
FIG. 8 is a diagram illustrating an example of an irradiation scheduled position in a case where the irradiation position deviation amount is detected during a treatment period.

Note that the irradiation scheduled position $C_0$ is preferably a plurality of positions separated from each other because it is not desirable to increase the number of measurement spots too much in order to reduce errors due to the curvature of the skin surface, the timing deviation from laser irradiation, and the like. For example, as illustrated in FIG. 8, the irradiation scheduled position $C_0$ is preferably the center, four corners, an intermediate position of each side, and the like of the exposed region of the skin surface, but is not limited thereto. In addition, the number of irradiation scheduled positions $C_0$ is preferably smaller than the number of divisions (M×N) of the initial correction table $T_0$ and the modification table $T_1$ to be described later from the viewpoint of shortening a measurement time, but is not limited thereto.

Furthermore, in a case where the luminance of the beam light is high at the time of this re-photographing, it is preferable to shorten an irradiation time of the beam light, shorten a shutter time of the imaging unit 40 to reduce an exposure time, or lower a gain of the imaging unit 40 in order to prevent halation.

Figures 9A, 9B, 9C:
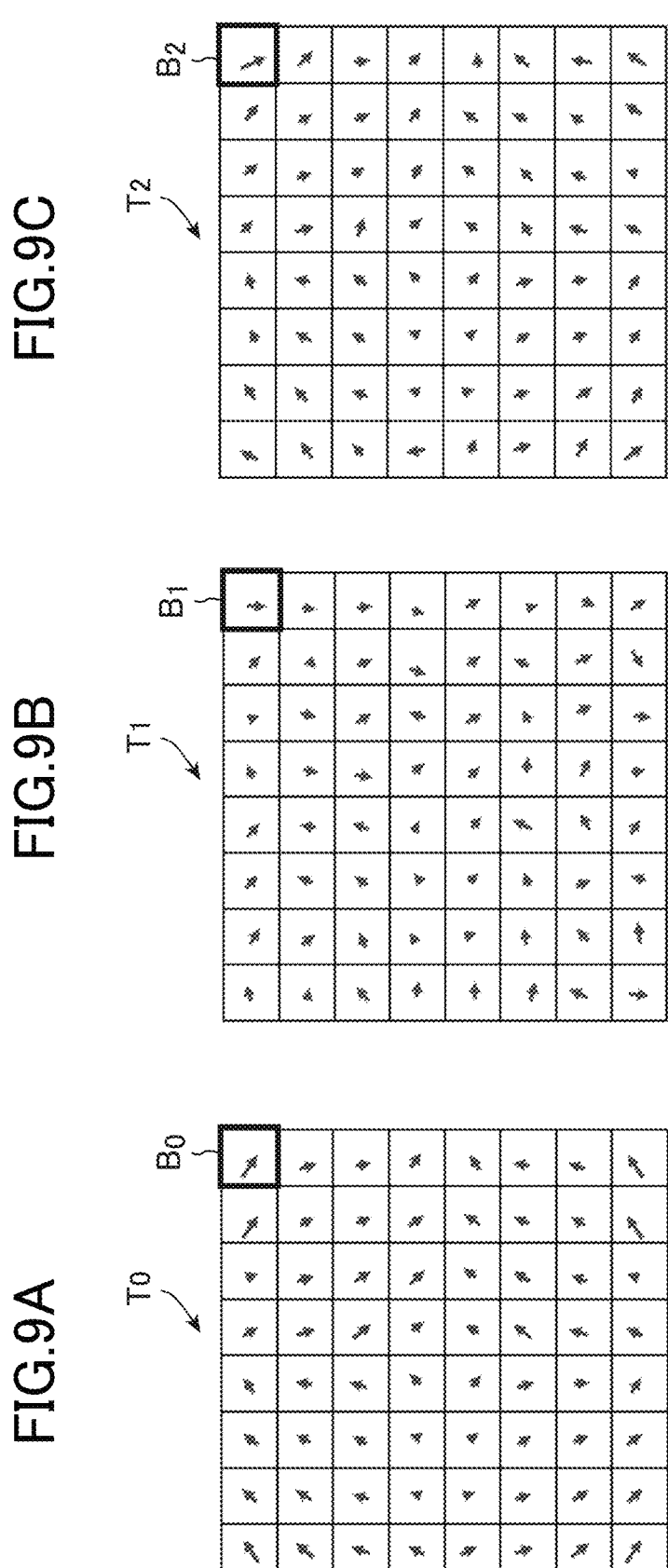
FIG. 9A is a diagram illustrating an image of an initial correction table.
FIG. 9B is a diagram illustrating an image of a modification table.
FIG. 9C is a diagram illustrating an image of a modified correction table.

The irradiation position deviation amount detection unit 116 is configured to store the irradiation position deviation amount detected by the above detection process in the storage unit 130. Specifically, as illustrated in FIGS. 9A and 9B, the irradiation position deviation amount detection unit 116 is configured to divide the treatment target region (the exposed region of the skin surface or the reflection plate) into M×N blocks (scan ranges), generate the initial correction table $T_0$ or the modification table $T_1$ by assigning the irradiation position deviation amount to each of these blocks, and store the initial correction table $T_0$ or the modification table $T_1$ in the storage unit 130. Here, both M and N are any integer of 1 or more, and M and N may be different numbers or the same number. In addition, the number of blocks of the initial correction table $T_0$ and the number of blocks of the modification table $T_1$ are preferably the same, but are not limited thereto. For example, the number of storage regions (the number of blocks) of the initial correction table $T_0$ may be divided more finely than the modification table $T_1$.

Here, the initial correction table $T_0$ is a correction table created at the time of factory shipment, overhaul, repair, or the like of the hair removal device 1. As illustrated in FIG. 9A, the initial correction table $T_0$ has a plurality of (M×N) storage regions, and is configured to be able to record, in each storage region, an initial correction amount in the corresponding block of the treatment target region. The irradiation position deviation amount stored in each storage region of the initial correction table $T_0$ has information on a deviation direction and a deviation amount, for example, as illustrated as a vector in FIG. 9A.

The modification table $T_1$ is a correction table newly created to correct a residual deviation of the initial correction table $T_0$ in a state in which the initial correction table $T_0$ exists. As illustrated in FIG. 9B, the modification table $T_1$ has the same number (M×N) of storage regions as the number of divisions of the treatment target region, and is configured to be able to record, in each storage region, the irradiation position deviation amount ($\Delta X$, $\Delta Y$) in the corresponding block of the treatment target region. The irradiation position deviation amount stored in each storage region of the modification table $T_1$ has information on a deviation direction and a deviation amount similarly to the initial correction table $T_0$. Since the correction amount (irradiation position deviation amount) in the modification table $T_1$ is a correction value for correcting the residual deviation of the initial correction table $T_0$ as described above, the correction amount is typically smaller than the correction amount (irradiation position deviation amount) in the initial correction table $T_0$.

In generating the initial correction table $T_0$ and the modification table $T_1$, in a case where the irradiation position deviation amount is not detected for all the divided regions (blocks), a value (interpolated irradiation position deviation amount) interpolated using the irradiation position deviation amount of the block in which the irradiation position deviation amount is detected may be recorded for the block in which the irradiation position deviation amount is not detected.

The correction condition creation unit 118 is configured to specify a correction amount of a guide position of the beam light by the irradiation position control mechanism 30 by using the irradiation position deviation amount ($\Delta X$, $\Delta Y$) detected by the irradiation position deviation amount detection unit 116. Specifically, the correction condition creation unit 118 is configured to generate the modified correction table $T_2$ by combining the initial correction table $T_0$ and the modification table $T_1$ (that is, modifying the initial correction table $T_0$ using the modification table $T_1$), and store the modified correction table $T_2$ in the storage unit 130. Note that the modified correction table $T_2$ may not be stored as a memory, and may be generated (calculated) using the initial correction table $T_0$ and the modification table $T_1$ every time.

In a case where the modified correction table $T_2$ is already stored in the storage unit 130, a process of changing (rewriting) the modified correction table $T_2$ every time the initial correction table $T_0$ or the modification table $T_1$ is updated is executed.

The modified correction table $T_2$ has the same number (M×N) of storage regions as the initial correction table $T_0$ and the modification table $T_1$, and is configured to be able to record, in each storage region (for example, a block $B_2$ illustrated in FIG. 9C), a modified correction amount generated by combining the initial correction amount stored in the corresponding block (for example, a block $B_0$ illustrated in FIG. 9A) of the initial correction table $T_0$ and the irradiation position deviation amount stored in the corresponding block (for example, a block $B_1$ illustrated in FIG. 9B) of the modification table $T_1$. Note that the number of storage regions (the number of blocks) of the modified correction table 12 does not have to be the same as that of the initial correction table $T_0$ and the modification table $T_1$, and, for example, the modified correction table 12 may be divided more finely than the initial correction table $T_0$ and/or the modification table $T_1$. In a case where the numbers of storage regions (the numbers of blocks) of the respective tables are different, a value interpolated using a value of an adjacent block may be used.

Note that the correction condition creation unit 118 may be configured to generate a statistical modification table $T_1$ by performing optional processing such as an averaging process using a plurality of the modification tables $T_1$ accumulated in the storage unit 130, and generate the modified correction table 12 by using the statistical modification table $T_1$.

In addition, the correction condition creation unit 118 may be configured to determine whether or not the irradiation position deviation amount (ΔX, ΔY) detected by the irradiation position deviation amount detection unit 116 exceeds a predetermined correctable range, and execute a warning process of reporting an error by an alarm sound, display, or the like when determining that the irradiation position deviation amount exceeds the predetermined correctable range.

The control mechanism drive control unit 122 is configured to control the irradiation position control mechanism 30 such that the pores specified by the pore specification unit 112 of the main control unit 110 are sequentially irradiated with the beam light from the light source unit 20 one by one.

Specifically, the control mechanism drive control unit 122 is configured to sequentially correct each guide position of the beam light (the irradiation scheduled position $C_0$ of the beam light) emitted toward each pore specified by the pore specification unit 112 on the basis of each modified correction amount stored in the modified correction table 12, and sequentially control the inclination angles of the reflection mirror 32a of the Y-direction deflection unit 32 and the reflection mirror 34a of the X-direction deflection unit 34 such that the corrected guide position C' is sequentially irradiated with the beam light.

Figures 10A, 10B, 10C:
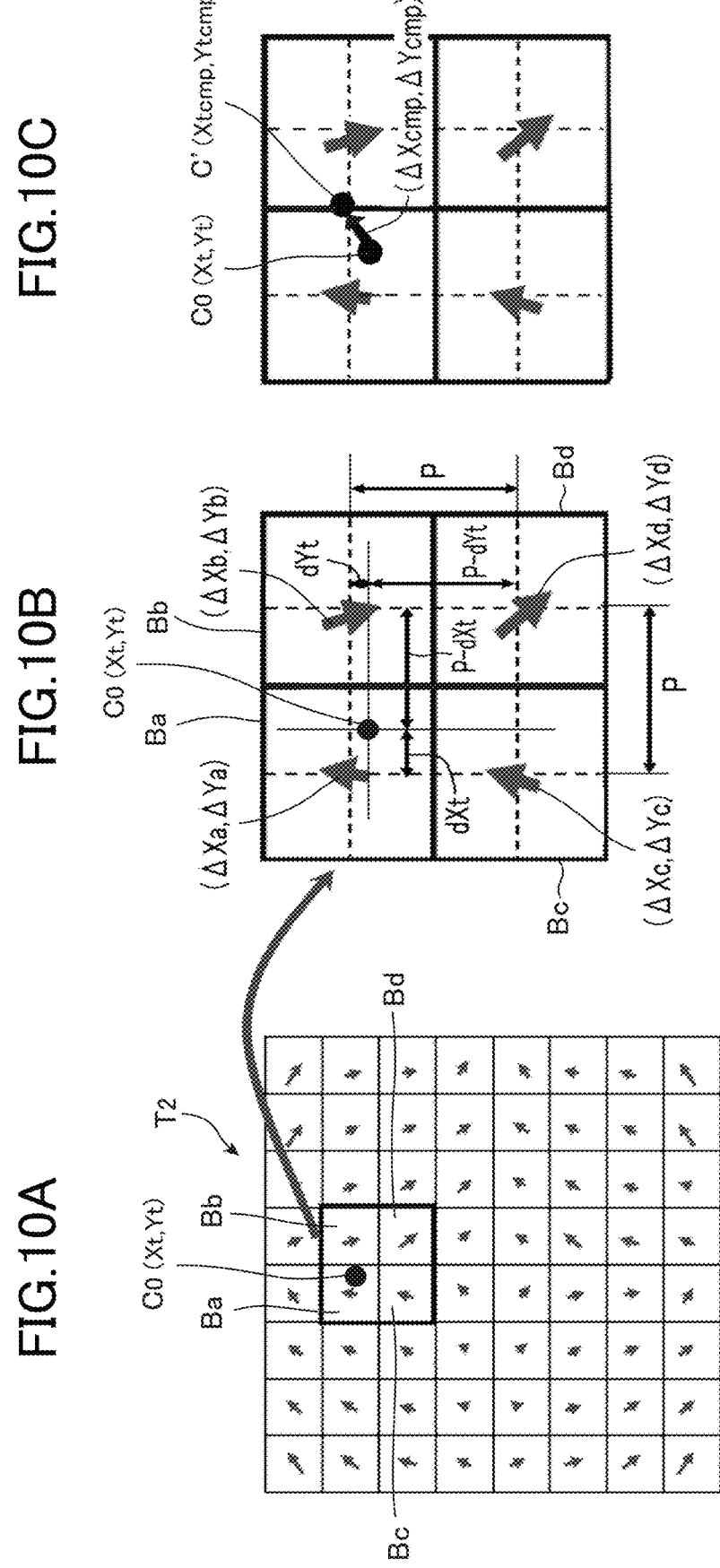
FIG. 10A is a diagram illustrating an image of the modified correction table.
FIG. 10B is a diagram illustrating a state in which four blocks surrounding the irradiation scheduled position of beam light are extracted.
FIG. 10C is a diagram illustrating an image of an interpolated correction amount at the irradiation scheduled position of beam light.

More specifically, the control mechanism drive control unit 122 is configured to first acquire a coordinate value (Xt, Yt) of the position (the irradiation scheduled position $C_0$ of the beam light) of each pore to be irradiated from the pore specification unit 112 as illustrated in FIG. 10A, and acquire modified correction amounts (ΔXa, ΔYa, ΔXb, ΔYb, ΔXc, ΔYc, ΔXd, ΔYd) of two or more blocks located around the coordinate value (Xt, Yt) (for example, four blocks Ba to Bd surrounding the coordinate value) from the latest modified correction table 12 stored in the storage unit 130 as illustrated in FIG. 10B.

In addition, as illustrated in FIG. 10C, the control mechanism drive control unit 122 is configured to calculate an interpolated correction amount (ΔXtcmp, ΔYtcmp) at the coordinate value (Xt, Yt) by interpolation from these four modified correction amounts (ΔXa, ΔYa, ΔXb, ΔYb, ΔXc, ΔYc, ΔXd, ΔYd) by various known methods such as a bilinear interpolation method. In FIG. 10B, "P" means a center-to-center distance between adjacent blocks. Moreover, "dXt" means a distance (difference) along an X-axis direction between the center of the block Ba and the block Bc and the coordinate value (Xt) of the irradiation scheduled position $C_0$ on an X-axis, and "P-dXt" means a distance (difference) along the X-axis direction between the center of the block Bb and the block Bd and the coordinate value (Xt) of the irradiation scheduled position $C_0$ on the X-axis. Furthermore, "dYt" means a distance (difference) along a Y-axis direction between the center of the block Ba and the block Bb and the coordinate value (Yt) of the irradiation scheduled position $C_0$ on a Y-axis, and "P-dYt" means a distance (difference) along the Y-axis direction between the center of the block Bc and the block Bd and the coordinate value (Yt) of the irradiation scheduled position $C_0$ on the Y-axis.

Furthermore, the control mechanism drive control unit 122 is configured to specify a coordinate value (Xtcmp, Ytcmp) of the corrected guide position C' on the basis of the interpolated correction amount (ΔXtcmp, ΔYtcmp) calculated as described above and the coordinate value (Xt, Yt) of the position of each pore acquired from the pore specification unit 112. Here, Xtcmp can be calculated by adding the correction amount (ΔXtcmp) in the X direction to the coordinate value (Xt) in the X-axis direction (Xtcmp=Xt+ΔXtcmp), and Ytcmp can be calculated by adding the correction amount (ΔYtcmp) in the Y direction to the coordinate value (Yt) in the Y-axis direction (Ytcmp=Yt+ΔYtcmp).

The control mechanism drive control unit 122 is configured to output a control signal to the irradiation position control mechanism 30 such that the coordinate value (Xtcmp, Ytcmp) specified as described above becomes the guide position C' of the beam light.

Such control of the control mechanism drive control unit 122 can be achieved, for example, by executing digital PID control using a dedicated inexpensive built-in microcomputer, but is not limited thereto.

Note that the control mechanism drive control unit 122 is not limited to the configuration in which the irradiation scheduled position $C_0$ is corrected using the interpolated correction amount obtained by interpolating the modified correction amounts of the two or more blocks located around the irradiation scheduled position $C_0$. For example, the irradiation scheduled position $C_0$ may be corrected using the modified correction amount of only one block including the irradiation scheduled position $C_0$.

As described above, the hair removal device 1 according to the present embodiment is configured to correct the guide position C' of the beam light by the irradiation position control mechanism 30 by using the irradiation position deviation amount between the irradiation scheduled position $C_0$ stored in advance in the storage unit 130 and the real irradiation position (the center C of the beam light) while specifying the position (X, Y) of each pore with high accuracy by the AI image recognition in the pore specification unit 112. Therefore, the hair removal device 1 according to the present embodiment can correct the deviation of the irradiation position caused by the mechanical factors in the irradiation position control mechanism 30 and the imaging unit 40, and can control the irradiation position control mechanism 30 such that the beam light is emitted toward each pore in a pinpoint manner. This makes it possible to irradiate only the pores with the beam light to improve efficiency and safety. In addition, since the hair removal device 1 according to the present embodiment directly images the actually emitted beam light by the imaging unit 40 and specifies the irradiation position deviation amount, there is an advantage that the highly accurate correction process can be achieved.

The light source control unit 124 is configured to control the light source unit 20 for each pore such that the beam light having the irradiation conditions specified by the irradiation condition specification unit 114 of the main control unit 110 is emitted from the light source unit 20. Specifically, the light source control unit 124 is configured to execute selection control of the light sources (first to third light sources) to emit light and output control of the light sources to emit light for each pore so as to obtain the beam light having the specified irradiation conditions (irradiation intensity, wavelength, and the like). Note that the light source control unit 124 may also be able to execute control of the illumination means (not illustrated) capable of emitting illumination light toward the opening 13.

The display control unit 126 is configured to be able to execute a process of transferring the real-time video (live image) captured by the imaging unit 40 onto the display panel 16 and displaying the video. As such a display control unit 126, various known control methods can be adopted, and thus a detailed description thereof is omitted.

[Irradiation Position Correction Method]

Figure 11:
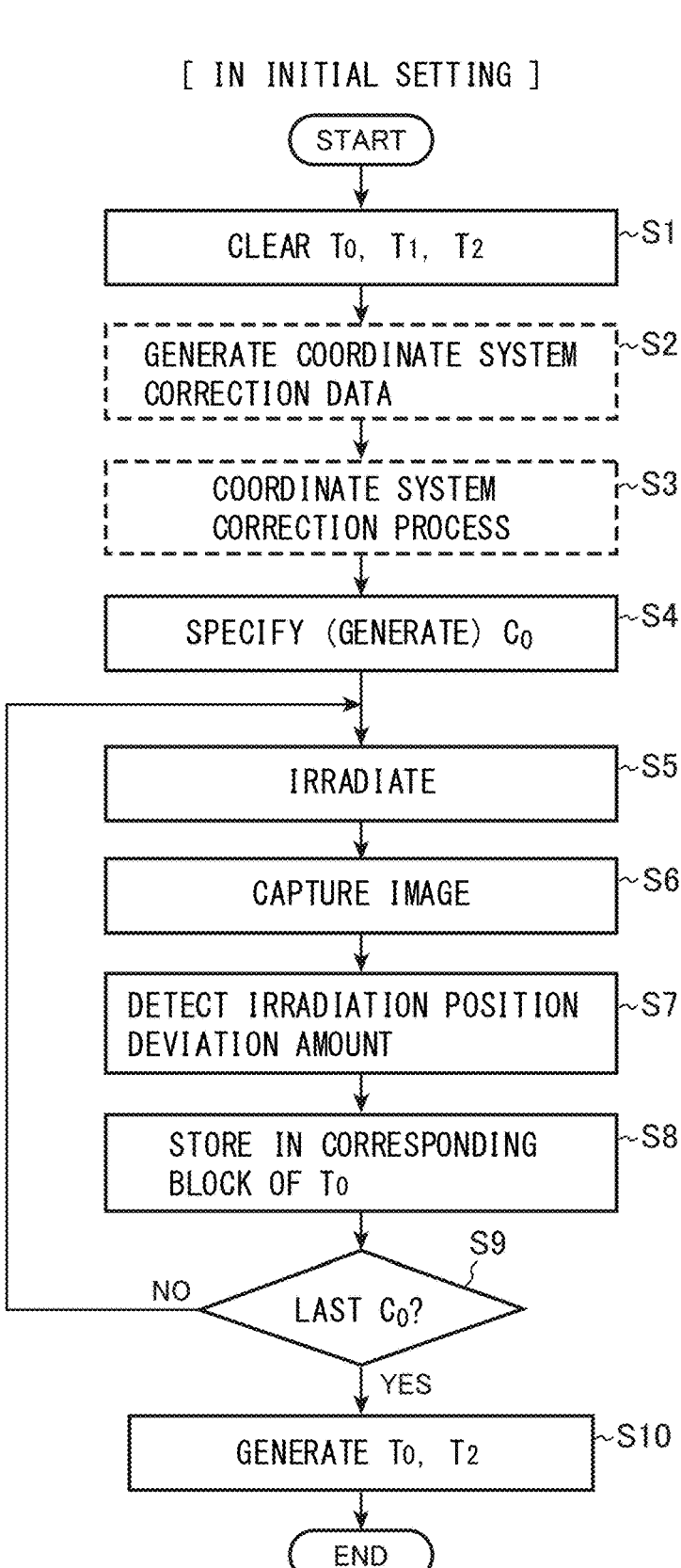
FIG. 11 is a flowchart schematically illustrating a flow of an irradiation position correction process (an irradiation position correction method at the time of initial setting) according to the embodiment of the present invention.
Figure 12:
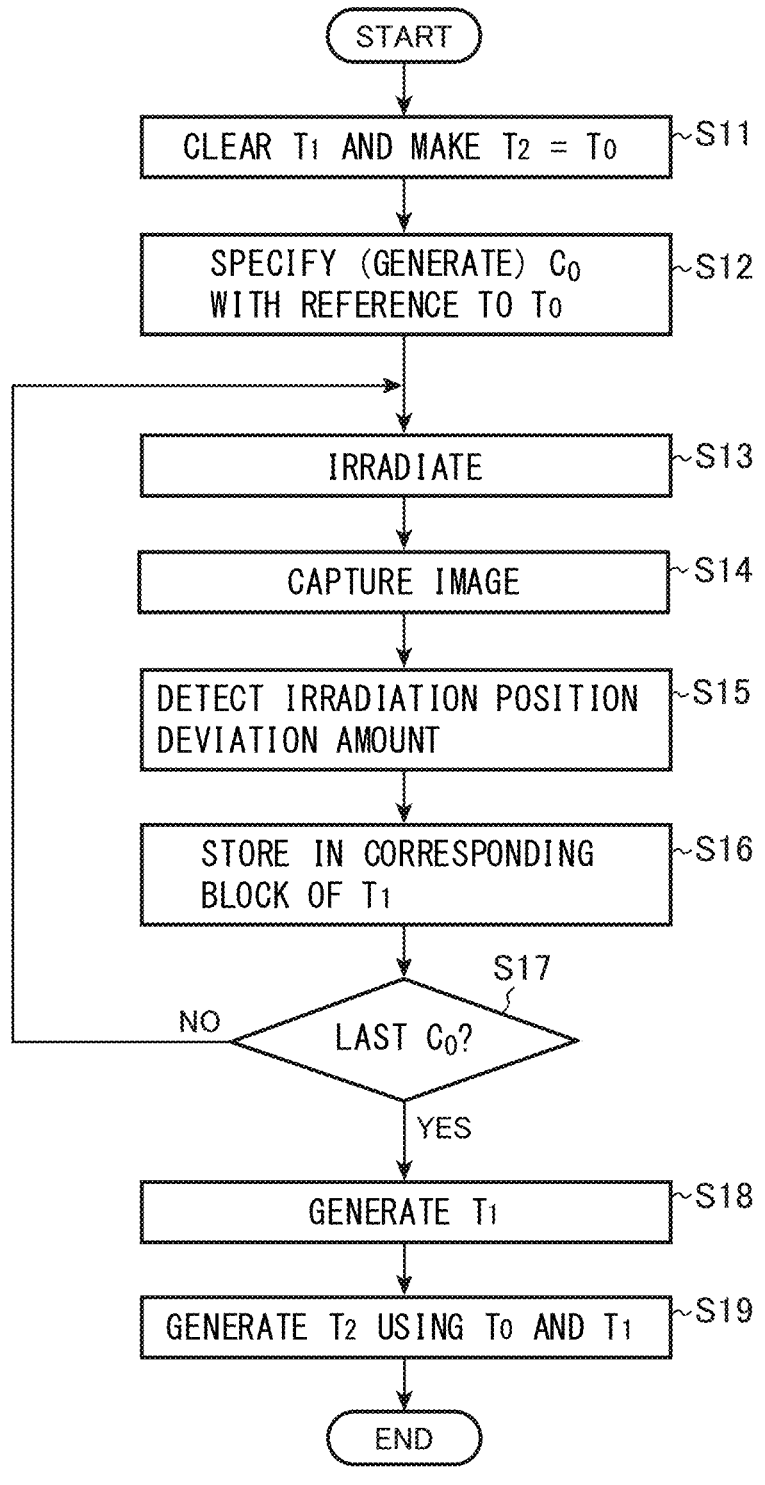
FIG. 12 is a flowchart schematically illustrating a flow of the irradiation position correction process (the irradiation position correction method at the time of correction (outside of the treatment period) after the initial setting) according to the embodiment of the present invention.
Figure 13:
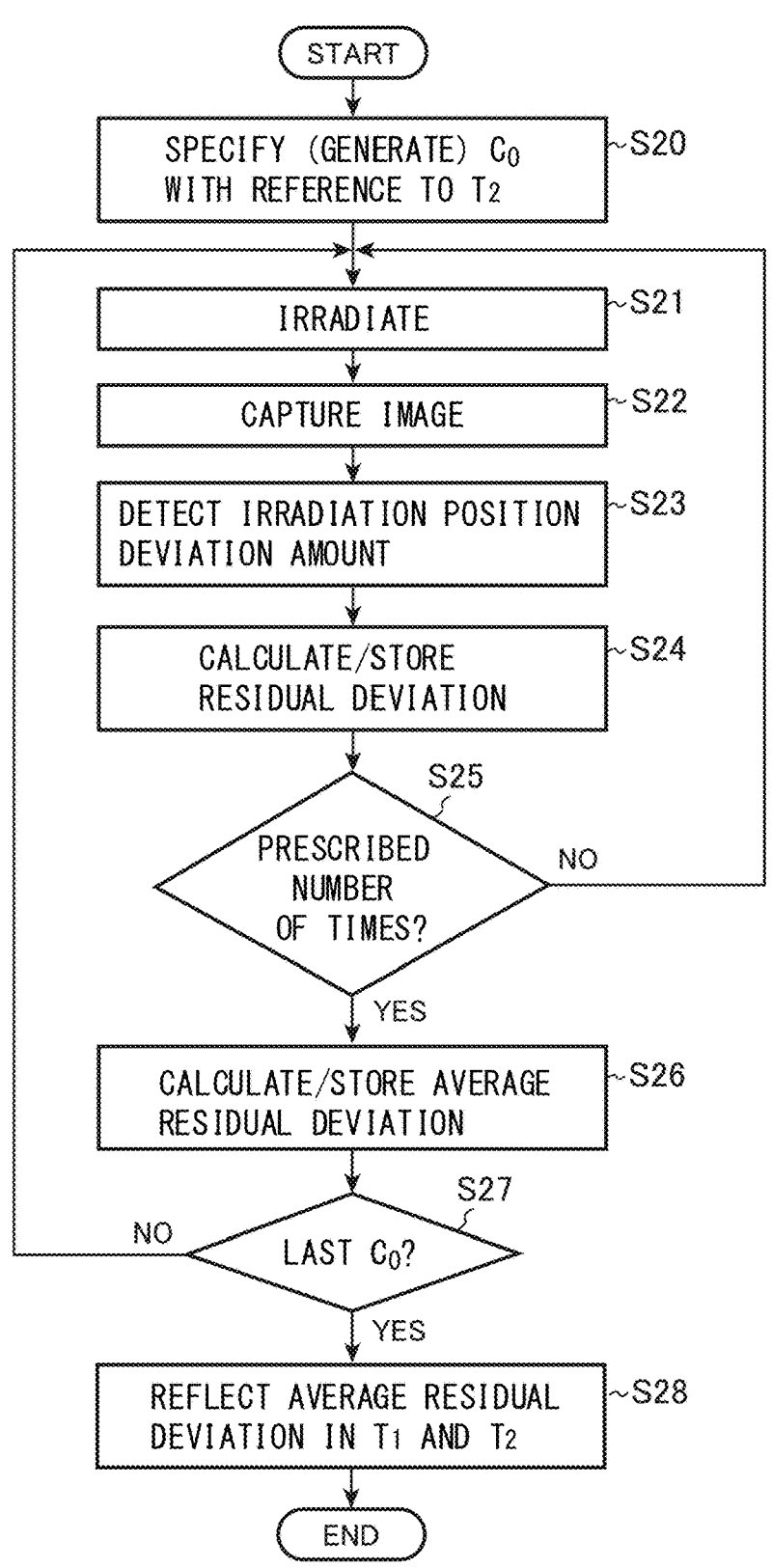
FIG. 13 is a flowchart schematically illustrating a flow of the irradiation position correction process (the irradiation position correction method at the time of correction (during the treatment period) after the initial setting) according to the embodiment of the present invention.

Next, an irradiation position correction method using the hair removal device 1 according to the present embodiment will be described with reference to FIGS. 11 to 13. The irradiation position correction method according to the present embodiment is schematically an irradiation position correction method for correcting the irradiation position of the light emitted from the light source, and is executed in any one or some of outside of the treatment period (for example, at the time of factory shipment, overhaul, repair, and standby) and during the treatment period (during the actual hair removal treatment for the pores). As described above, outside of the treatment period, the irradiation position correction process is executed in a state in which the reference reflection plate 60 and the like are disposed facing the opening 13 of the head portion 12 so as to be relatively unmovable. On the other hand, as described above, during the treatment period, the irradiation position correction process is executed in a state in which the skin surface to be treated is disposed facing the opening 13 of the head portion 12.

[Irradiation Position Correction Method in Initial Setting]

First, the irradiation position correction method at the time of initial setting will be described with reference to FIG. 11. Since it is assumed that there is a large mechanical deviation at the time of initial setting (at the time of factory shipment, overhaul, repair, etc.), the initial correction table $T_0$, the modification table $T_1$, and the modified correction table 12 are cleared even when stored in the storage unit 130 (S1: initialization step). In addition, in a case where the above-described coordinate system correction process (numerical correction) has not been performed or needs to be performed again, the coordinate system correction data is generated by the above-described coordinate system correction process (numerical correction) (S2), and the correction process is executed (S3) as necessary. Then, as described above, the region of the reference reflection plate 60 is divided into a plurality of regions (preferably equally divided), and the center of each of the divided regions is specified (generated) as the coordinates of the irradiation scheduled position $C_0$ (S4: irradiation scheduled position specification step).

Then, when the irradiation scheduled position $C_0$ is specified, the control mechanism drive control unit 122 drives the irradiation position control mechanism 30, and the light source unit 20 emits the beam light toward the irradiation scheduled position $C_0$ (S5: irradiation step).

In addition, while the irradiation step is being executed, the predetermined region (the irradiation state of the beam light) including the beam light emitted toward the irradiation scheduled position $C_0$ is imaged by the above-described function of the imaging unit 40 (S6: imaging step), and the detection process of the irradiation position deviation amount ($\Delta X$, $\Delta Y$) between the irradiation scheduled position $C_0$ of the beam light and the real irradiation position of the actually emitted beam light (the center C of the beam light) is executed by the above-described function of the irradiation position deviation amount detection unit 116 (S7: irradiation position deviation amount detection step). Then, the irradiation position deviation amount ($\Delta X$, $\Delta Y$) detected at the irradiation position deviation amount detection step is stored in the corresponding block (corresponding storage region) of the initial correction table $T_0$ (S8: irradiation position deviation amount storage step).

Thereafter, in a case where the irradiation scheduled position $C_0$ to be treated next exists (NO at S9), the respective steps S5 to S8 described above are executed for the irradiation scheduled position $C_0$ to be treated next. On the other hand, in a case where there is no irradiation scheduled position $C_0$ to be treated next (YES at S9), the initial correction table $T_0$ is generated (newly created or updated) by the above-described function of the irradiation position deviation amount detection unit 116, and is stored in the storage unit 130. In addition, since the modification table $T_1$ has already been cleared and does not exist, the modified correction table $T_2$ is rewritten to the same contents as the initial correction table $T_0$ (S10: initial correction table generation step, modified correction table generation step). Then, the modified correction table $T_2$ generated at the modified correction table generation step (S10) is used for the hair removal treatment in the next and subsequent times (for example, the next cycle).

[Irradiation Position Correction Method in Correction (Outside of Treatment Period) after Initial Setting]

Next, the irradiation position correction method performed at an optional timing (for example, every several days, at the time of power startup, after completion of the prescribed number of times of treatment, and after completion of every treatment) after the initial setting will be described with reference to FIG. 12. At this timing, there is a high possibility that a large deviation does not occur as compared with that in the initial setting. Therefore, the irradiation scheduled position $C_0$ is specified (generated) using the coordinate system corrected with reference to the initial correction table $T_0$, the residual deviation amount at the position is measured to generate the modification table $T_1$, and the modified correction table $T_2$ is modified using the initial correction table $T_0$ and the modification table $T_1$.

Specifically, first, the modified correction table $T_2$ stored in the storage unit 130 is made identical with the initial correction table $T_0$ (S11). In a case where the modification table $T_1$ is stored in the storage unit 130, the modification table $T_1$ is also cleared. If necessary, the coordinate system correction process (not illustrated) is also executed. Then, the irradiation scheduled position $C_0$ is specified (generated) with reference to the initial correction table $T_0$ stored in the storage unit 130 (S12: irradiation scheduled position specification step).

Thereafter, similarly to the initial setting, the irradiation step (S5), the imaging step (S6), and the irradiation position deviation amount detection step (S7) described above are executed to detect the irradiation position deviation amount ($\Delta X$, $\Delta Y$) between the irradiation scheduled position $C_0$ of the beam light and the real irradiation position of the actually emitted beam light (the center C of the beam light) (S13 to S15). Then, the irradiation position deviation amount detected at the irradiation position deviation amount detection step is stored in the corresponding block (corresponding storage region) of the modification table $T_1$ (S16: irradiation position deviation amount storage step).

Thereafter, in a case where the irradiation scheduled position $C_0$ to be treated next exists (NO at S17), the respective steps S13 to S16 described above are executed for the irradiation scheduled position $C_0$ to be treated next. On the other hand, in a case where there is no irradiation scheduled position $C_0$ to be treated next (YES at S17), the modification table $T_1$ is generated (newly created or updated) by the above-described function of the irradiation position deviation amount detection unit 116, and is stored in the storage unit 130 (S18: modification table generation step). In addition, the modified correction table 12 is generated (modified) using the initial correction table $T_0$ stored in the storage unit 130 and the modification table $T_1$ generated at the modification table generation step (S18) by the above-described function of the correction condition creation unit 118 (S19: modified correction table generation step). Then, the modified correction table 12 generated at the modified correction table generation step (S19) is used for the hair removal treatment in the next and subsequent times (for example, the next cycle).

[Irradiation Position Correction Method in Correction (during Treatment Period) after Initial Setting]

Next, the irradiation position correction method performed during the treatment period after the initial setting will be described with reference to FIG. 13.

First, the irradiation scheduled position $C_0$ is specified (generated) with reference to the modified correction table 12 stored in the storage unit 130 (S20: irradiation scheduled position specification step). If necessary, the coordinate system correction process (not illustrated) is also executed. Thereafter, similarly to the initial setting, the irradiation step (S5), the imaging step (S6), and the irradiation position deviation amount detection step (S7) described above are executed to detect the irradiation position deviation amount ($\Delta X$, $\Delta Y$) between the irradiation scheduled position $C_0$ of the beam light and the real irradiation position of the actually emitted beam light (the center C of the beam light) (S21 to S23). In addition, the residual deviation amount is calculated by obtaining the difference between the detected irradiation position deviation amount and the irradiation position deviation amount stored in the modified correction table 12, and is stored in the storage unit 130 (S24: residual deviation amount calculation step).

In the irradiation position correction during the treatment period, unlike the irradiation position correction at the time of the initial setting or outside of the treatment period described above, the irradiation step (S21), the imaging step (S22), the irradiation position deviation amount detection step (S23), and the residual deviation amount calculation step (S24) are executed for the same irradiation scheduled position $C_0$ a plurality of times until reaching the specified number of times (S25) to calculate an average value of the residual deviation amounts at the irradiation scheduled position $C_0$, which is stored in the storage unit 130 (S26: average residual deviation amount calculation step). As described above, by using the average value of the residual deviation amounts without directly adopting the residual deviation amount obtained by performing the imaging once, it is possible to reduce the influence of measurement errors such as the position deviation due to the curvature of the skin surface and the time lag (timing deviation) between the imaging and the beam light irradiation.

Thereafter, in a case where the irradiation scheduled position $C_0$ to be treated next exists (NO at S27), the respective steps S21 to S26 described above are executed for the irradiation scheduled position $C_0$ to be treated next. On the other hand, in a case where there is no irradiation scheduled position $C_0$ to be treated next (YES at S27), the modification table $T_1$ and the modified correction table $T_2$ are generated (modified) by reflecting the average value of the residual deviation amounts calculated at the average residual deviation amount calculation step (S26) in the modification table $T_1$ and the modified correction table 12 (S28: modification table generation step, modified correction table generation step). Then, the modified correction table 12 generated at the modified correction table generation step (S28) is used for the hair removal treatment in the next and subsequent times (for example, the next cycle).

[Epilation Method]

Figure 14:
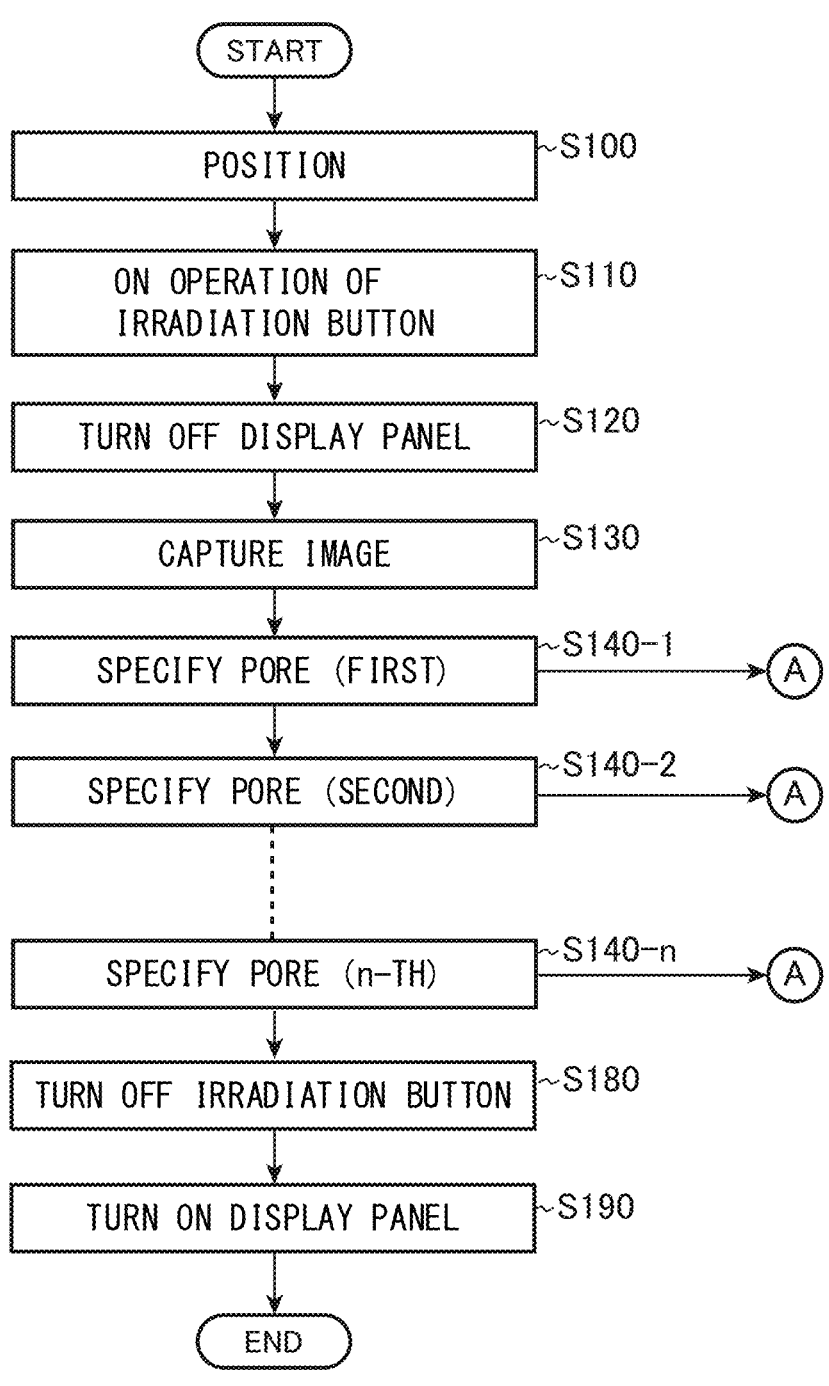
FIG. 14 is a flowchart schematically illustrating a flow of a hair removal method according to the embodiment of the present invention.
Figure 15:
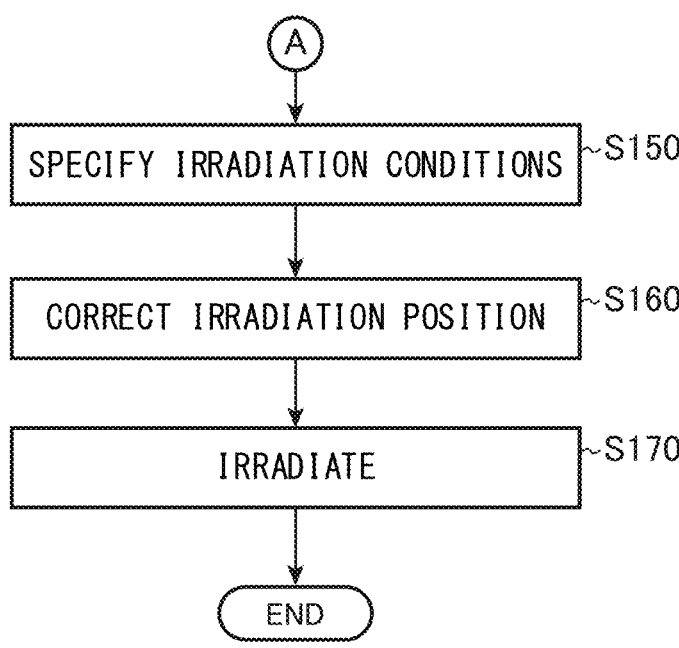
FIG. 15 is a flowchart schematically illustrating a flow of processing for each pore.

Next, a hair removal method using the hair removal device 1 according to the present embodiment will be described with reference to FIGS. 14 and 15. FIG. 14 is a flowchart schematically illustrating an overall flow of the hair removal method according to the present embodiment, and FIG. 15 is a flowchart schematically illustrating a flow of processing for one pore specified by the pore specification unit 112. Note that the hair removal method described below is executed by a program, learning result data, and the like stored in the storage unit 130 of the hair removal device 1.

In starting the hair removal method according to the present embodiment, first, the hair removal device 1 is activated by turning ON a main power source of the hair removal device 1. When the hair removal device 1 is activated, the real-time video (live image) captured by the imaging unit 40 is displayed on the display panel 16. As a result, even in a state in which the opening 13 is pressed against the skin (during shot movement by a person), the treatment target region can be visually recognized by the live image on the display panel 16. Note that the hair removal device 1 may be operated by a person to be treated himself/ herself or may be operated by a person different from the person to be treated (a medical worker or the like). Hereinafter, a person who operates the hair removal device 1 is referred to as a "user".

In a state in which the hair removal device 1 is activated, the user positions the hair removal device 1 such that the opening 13 of the housing 10 is located in the treatment target region (S100), and performs an ON operation of the irradiation button 18 after completion of the positioning (S110) as illustrated in FIG. 14. When the ON operation of the irradiation button 18 is performed, the display panel 16 is turned OFF (S120), and the treatment target region of the skin is imaged by the imaging unit 40 (S130). Then, the image data captured by the imaging unit 40 is transmitted to the main control unit 110 of the control unit 100, and by the above-described function of the pore specification unit 112 in the main control unit 110, the preprocessing is performed on the image data as necessary, and then the pores (pore candidates P) present in the treatment target region are sequentially specified (S140-1 to S140-n: pore specification step).

In parallel with the specification of the pores, the specification process of the irradiation conditions (irradiation intensity, wavelength, and the like) and the irradiation process are sequentially performed for the specified pores. That is, when the first pore candidate P is specified by the above-described function of the pore specification unit 112, the main control unit 110 executes the process of specifying the irradiation conditions and the like for the first pore candidate P independently of (in parallel with) the process of specifying the second pore candidate P as illustrated in FIG. 15. In addition, when the second pore candidate P is specified, the main control unit 110 executes the process of specifying the irradiation conditions and the like for the second pore candidate P independently of (in parallel with) the process of specifying the irradiation conditions for the first pore candidate P and the process of specifying the third pore candidate P. The main control unit 110 executes such parallel processing up to the last (n-th) pore candidate P. As described above, by the sequence in which the pore recognition and the beam light irradiation are performed in parallel, it is possible to secure a time for the recognition process without prolonging the time of one cycle.

The specification of the irradiation conditions (irradiation intensity, wavelength, and the like) for each pore candidate P (S150: irradiation condition specification step) is executed by the above-described function of the irradiation condition specification unit 114 in the main control unit 110. In a case where it is determined that there is no corresponding standard model image in the irradiation condition specification step, it may be determined that the pore candidate P is not a pore, and the processing for the pore candidate P may be ended without moving to the next step (without executing the irradiation of the pore candidate P with the beam light).

When the irradiation conditions for each pore candidate P are specified, the control mechanism drive control unit 122 drives the irradiation position control mechanism 30 so as to irradiate the pore candidate P with the beam light from the light source unit 20. At this time, by the above-described function of the control mechanism drive control unit 122, the guide position of the beam light by the irradiation position control mechanism 30 is corrected using the latest modified correction table $T_2$ stored in advance in the storage unit 130 (S160: irradiation position correction step).

Thereafter, the pore candidate P is irradiated with the beam light having the irradiation conditions (irradiation intensity, wavelength, and the like) specified at the irradiation condition specification step from the light source unit 20 (S170: irradiation step). As a result, the hair root of the pore candidate P is heated and removed permanently or over a long period of time. Note that a time required to control the irradiation position varies depending on various conditions such as a moving distance, but is approximately several ms. In addition, an irradiation time of the beam light varies depending on various conditions such as the irradiation intensity, but is approximately several ms to several 10 ms. Since the irradiation conditions (irradiation intensity, wavelength, and the like) of the beam light at this time are the optimal irradiation conditions (irradiation intensity, wavelength, and the like) assigned to the most approximate standard model image, the irradiation conditions are effective against the pore candidate P, less harmful to and safe against the skin around the pore candidate P.

When the processing for all the pore candidates P is completed by executing the series of processes from S150 to S170 described above for the last (n-th) pore candidate P, the irradiation button 18 is turned into an OFF state (S180), and the real-time video (live image) captured by the imaging unit 40 is displayed on the display panel 16 again (S190) as illustrated in FIG. 14.

In addition, in a case where the above-described irradiation position correction method is executed during the treatment period, the modification table $T_1$ and the modified correction table 12 generated (modified) by the above-described irradiation position correction method are stored in the storage unit 130 at an optional timing (for example, a timing after completion of the processing for all the pore candidates P). Then, the modified correction table 12 stored in the storage unit 130 is used for the irradiation position correction step (S160) in the next and subsequent times (for example, the next cycle).

A cycle from the positioning (movement) of the hair removal device 1 to the completion of irradiation of all the pores in the treatment target region as described above is defined as one cycle. The hair removal treatment is performed by executing the cycle while sequentially moving the position over a desired treatment target region. In one cycle, a standard time from the ON operation of the irradiation button 18 to the completion of irradiation of the pores in the treatment target region (the treatment time of the hair removal device 1) is within 1 second when it is assumed that the number of pores is 30 or less and the irradiation/movement time is 20 ms, and is within 3 seconds when it is assumed that the number of pores is 100 or less and the irradiation/movement time is 20 ms. As described above, the hair removal device 1 according to the present embodiment can perform the hair removal treatment in an extremely short time.

[Advantages of Epilation Device According to Present Embodiment]

As described above, the hair removal device 1 according to the present embodiment includes the light source unit 20 including the light source, the irradiation position control mechanism 30 configured to guide the light emitted from the light source unit 20 to the irradiation scheduled position $C_0$, the imaging unit 40 configured to be able to image the predetermined region including the light emitted toward the irradiation scheduled position, and the irradiation position deviation amount detection unit 116 configured to detect the irradiation position deviation amount ($\Delta X$, $\Delta Y$) between the irradiation scheduled position $C_0$ and the real irradiation position of the light (the center C of the beam light), and is configured to correct the guide position of the light by the irradiation position control mechanism 30 by using the irradiation position deviation amount ($\Delta X$, $\Delta Y$) detected by the irradiation position deviation amount detection unit 116.

The hair removal device 1 according to the present embodiment configured as described above can correct the deviation of the irradiation position caused by the mechanical factors in the irradiation position control mechanism 30 and the imaging unit 40, and can control the irradiation position control mechanism 30 such that the beam light is emitted toward each pore in a pinpoint manner. In addition, this allows for irradiation of only the pores with the beam light, so that the efficiency and safety can be improved. Furthermore, since the actually emitted beam light is directly imaged by the imaging unit 40 to specify the irradiation position deviation amount ($\Delta X$, $\Delta Y$), the highly accurate correction process can be achieved.

MODIFICATION EXAMPLES

Although the preferred embodiment of the present invention has been described above, the technical scope of the present invention is not limited to the scope described in the above-described embodiment. Various modifications or improvements can be made in each embodiment described above.

For example, in the above-described embodiment, it has been described that the correction value, the irradiation position deviation amount, and the like are stored using the tables (the initial correction table $T_0$, the modification table $T_1$, and the modified correction table 12), but the present invention is not limited thereto. The correction value, the irradiation position deviation amount, and the like may be stored by any method such as mathematical expression expansion.

In the above-described embodiment, it has been described that the irradiation condition specification unit 114 specifies the irradiation conditions according to the pore size, the hair color, the color of the surrounding skin, and the like by classifying the cutout pore image CI into the standard model image. However, the present invention is not limited thereto, and a configuration may be adopted in which the irradiation conditions are not changed for each pore.

In the above-described embodiment, it has been described that the recognition of only the pores is performed once in the pore specification unit 112, and then the cutout pore image CI is cut out from the image data I in the irradiation condition specification unit 114. However, the present invention is not limited thereto, and by adding the inference values of the pore size, the hair color, the surrounding skin color, and the like to the objective function in the pore specification unit 112, classification and position inference of the image similar to the standard model image may be performed from the images of the small regions (cells) obtained by dividing the image data I, and the pore position, pore size, hair color, and surrounding skin color may be directly acquired.

In the above-described embodiment, it has been described that the cutout pore image CI is classified by the AI image recognition, but the present invention is not limited thereto. A method of converting into numerical values feature amounts of the pore size, the hair color, and the skin color around the pore of the pore candidate P included in the cutout pore image CI and comparing the feature amounts with feature amounts of standard models registered in advance in a database to classify the cutout pore image CI into the most approximate standard model can also be optionally adopted.

In the above-described embodiment, it has been described that the hair removal device 1 includes the trained learner (neural network) that has been trained for performing the AI image recognition related to the pore specification and the pore image classification, but the present invention is not limited thereto. A configuration may be adopted in which the trained learner is provided in another device connected to the hair removal device 1 so as to be capable of data communication via a high-speed communication network, and communication is performed in real time between each hair removal device 1 and the other device (cloud computing). In addition, in the hair removal device 1 or the other device, machine learning (AI learning process) may be performed using the image data I of the treatment target region TA as input data and the certainty factor to be a pore or the coordinates as reference data on the basis of a predetermined learning program, or learning data with higher recognition accuracy may be shared in real time by uploading images captured by a plurality of the hair removal devices 1 via a cloud to increase the number of acquired images in an accelerated manner.

In the above-described embodiment, it has been described that the dichroic mirror 17 is provided inside the head portion 12, the light source unit 20 is disposed on the reflection surface side of the dichroic mirror 17, and the imaging unit 40 is disposed on the transmission surface side, but the present invention is not limited thereto. For example, the imaging unit 40 may be disposed on the reflection surface side of the dichroic mirror 17, and the light source unit 20 may be disposed on the transmission surface side. In addition, a configuration may be adopted in which the dichroic mirror 17 is not provided. Examples of the configuration in which the dichroic mirror 17 is not provided include, but are not limited to, a configuration in which the imaging unit 40 is disposed perpendicular to the opening 13 (the treatment target region of the skin) and the beam light from the light source unit 20, which has been deflected by the irradiation position control mechanism 30, is emitted to the opening 13 (the treatment target region of the skin) from an oblique direction, and a configuration in which the opening 13 (the treatment target region of the skin) is photographed by the imaging unit 40 from an oblique direction and the beam light from the light source unit 20, which has been deflected by the irradiation position control mechanism 30, is emitted to the opening 13 (the treatment target region of the skin) from an oblique direction.

It is apparent from the description of the claims that the above modifications are included in the scope of the present invention.

REFERENCE SIGNS LIST

1 Epilation Device
10 Housing
11 Grip Portion
12 Head Portion
13 Opening
14 Cover Member
15 Movement Detection Sensor
16 Display Panel
17 Dichroic Mirror
18 Irradiation Button
20 Light Source Unit
30 Irradiation Position Control Mechanism
32 Y-Direction Deflection Unit
32a Reflection mirror
32b Drive Unit
34 X-Direction Deflection Unit
34a Reflection mirror
34b Drive Unit
40 Imaging Unit
50 Epilation Device Placement Stand
52 Fitting Recess
100 Control Unit
102 External Interface
104 External Interface
106 External Interface
110 Main Control Unit
112 Pore Specification Unit
114 Irradiation Condition Specification Unit
116 Irradiation Position Deviation Amount Detection Unit 118 Correction Condition Creation Unit
122 Control Mechanism Drive Control Unit
124 Light Source Control Unit
126 Display Control Unit
130 Storage Unit
C Center of Beam Light
$C_0$ Irradiation Scheduled Position of Beam Light
$T_0$ Initial Correction Table
$T_1$ Modification Table
$T_2$ Modified Correction Table

The invention claimed is:

1. A hair removal device that performs hair removal treatment with light emitted from a light source, the hair removal device comprising:

a light source unit including the light source;

an irradiation position control mechanism configured to guide the light emitted from the light source unit to an irradiation scheduled position;

an imaging unit configured to be able to image a predetermined region including the light emitted toward the irradiation scheduled position; and an irradiation position deviation amount detection unit configured to detect an irradiation position deviation amount between the irradiation scheduled position and a real irradiation position of the light, the hair removal device being configured to correct a guide position of the light by the irradiation position control mechanism by using the irradiation position deviation amount detected by the irradiation position deviation amount detection unit, the irradiation position deviation amount detection unit is configured to generate a modification table by dividing a treatment target region into a plurality of blocks and assigning the irradiation position deviation amount to each of the blocks.

2. The hair removal device according to claim 1, wherein the irradiation position deviation amount detection unit is configured to specify a center of the light by using irradiation state image data captured by the imaging unit and specify the center of the light as the real irradiation position of the light.

3. The hair removal device according to claim 1, further comprising a correction condition creation unit configured to specify a correction amount of the guide position of the light by the irradiation position control mechanism by using the irradiation position deviation amount detected by the irradiation position deviation amount detection unit.

4. The hair removal device according to claim 1, wherein the correction condition creation unit is configured to generate a modified correction table on a basis of an initial correction table that stores an initial correction amount of the guide position and the modification table generated by the irradiation position deviation amount detection unit.

5. The hair removal device according to claim 4, wherein the correction condition creation unit is configured to generate a statistical modification table by using a plurality of the modification tables and generate the modified correction table by using the statistical modification table.

6. The hair removal device according to claim 4, further comprising a control mechanism drive control unit configured to control the irradiation position control mechanism, wherein the control mechanism drive control unit is configured to correct the guide position of the light by the irradiation position control mechanism on a basis of the modified correction table.

7. An irradiation position correction method for correcting an irradiation position of light emitted from a light source, the irradiation position correction method comprising:

an irradiation step of guiding the light to an irradiation scheduled position and irradiating the irradiation scheduled position;

an imaging step of imaging a predetermined region including the light emitted toward the irradiation scheduled position; and an irradiation position deviation amount detection step of detecting an irradiation position deviation amount between the irradiation scheduled position and a real irradiation position of the light, a guide position of the light being corrected using the irradiation position deviation amount detected at the irradiation position deviation amount detection step, the irradiation position deviation amount detection step is generated a modification table by dividing a treatment target region into a plurality of blocks and assigning the irradiation position deviation amount to each of the blocks.

8. The irradiation position correction method according to claim 7, wherein the irradiation step, the imaging step, and the irradiation position deviation amount detection step are executed during a treatment period in which hair removal treatment is performed by the light emitted from the light source.

9. The irradiation position correction method according to claim 7, wherein the irradiation step, the imaging step, and the irradiation position deviation amount detection step are executed outside of a treatment period in which hair removal treatment is performed by the light emitted from the light source.

* * * * *